(12) United States Patent
Jølck et al.

(10) Patent No.: US 9,161,993 B2
(45) Date of Patent: Oct. 20, 2015

(54) CHARGE TRIGGERING OF SELF-ORGANIZED NANOPARTICLES

(75) Inventors: Rasmus Irming Jølck, Valby (DK); Jonas Rosager Henriksen, Allerød (DK); Torben Gjetting, Jyllinge (DK); Thomas Lars Andresen, Vanløse (DK)

(73) Assignee: Danmarks Tekniske Universitet, Lyngby (DK)

( * ) Notice: Subject to any disclaimer, the term of this patent is extended or adjusted under 35 U.S.C. 154(b) by 0 days.

(21) Appl. No.: 14/117,881

(22) PCT Filed: May 16, 2012

(86) PCT No.: PCT/DK2012/050174
§ 371 (c)(1),
(2), (4) Date: Nov. 15, 2013

(87) PCT Pub. No.: WO2012/155920
PCT Pub. Date: Nov. 22, 2012

(65) Prior Publication Data
US 2014/0328897 A1    Nov. 6, 2014

Related U.S. Application Data

(60) Provisional application No. 61/486,420, filed on May 16, 2011.

(30) Foreign Application Priority Data

May 16, 2011 (EP) .................................... 11166163
Mar. 16, 2012 (EP) .................................... 12159792

(51) Int. Cl.
*A61K 47/48* (2006.01)
*A61K 31/282* (2006.01)
(Continued)

(52) U.S. Cl.
CPC ......... *A61K 47/48838* (2013.01); *A61K 9/1272* (2013.01); *A61K 9/145* (2013.01);
(Continued)

(58) Field of Classification Search
CPC .................................................. A61K 47/48238
See application file for complete search history.

(56) References Cited

U.S. PATENT DOCUMENTS 5,474,765 A * 12/1995 Thorpe .................... 424/78.17
6,087,325 A *  7/2000 Meers et al. .................. 530/300
(Continued)

FOREIGN PATENT DOCUMENTS

| AU | 2005227364 | 11/2005 |
|----|------------|---------|
| WO | WO9304673  | 3/1993  |

(Continued)

OTHER PUBLICATIONS

TA Aguilera, ES Olson, MM Timmers, T Jiang, RY Tsien. "Systemic in vivo Distribution of Activatable Cell Penetrating Peptides is Superior to that of Cell Penetrating Peptides." Integrative Biology, vol. 1, 2009, pp. 371-381 (along with initial cover page).*

(Continued)

*Primary Examiner* — Isaac Shomer
(74) *Attorney, Agent, or Firm* — McHale & Slavin, P.A.

(57) ABSTRACT

The present application discloses a nanoparticle comprising compounds of the formula A-B-C(-D), wherein A designates an anchoring moiety having self-organizing properties in relation to the nanoparticle; B designates a cleavable linker; C designates an anionic moiety having a net charge of at least −2 at pH 6.0; and D, which is optional, designates a polymer moiety which induces long circulating properties of the nanoparticle in mammalian tissue; and wherein the average net charge of the compounds is at least −1 at pH 6.0. The application also discloses the individual compounds of the formula A-B-C(-D) as well as a drug delivery system comprising the self-organized nanoparticle having included in the interior thereof one or more pharmaceutically active agents and/or diagnostically relevant species, and a method of treating a cancerous or inflammatory condition in a mammal, involving the administration of the drug delivery system to the mammal.

16 Claims, 10 Drawing Sheets

(51) Int. Cl.
*A61K 31/7088* (2006.01)
*A61K 9/127* (2006.01)
*A61K 9/14* (2006.01)

(52) U.S. Cl.
CPC .......... *A61K 31/282* (2013.01); *A61K 31/7088* (2013.01); *A61K 47/48053* (2013.01); *A61K 47/48215* (2013.01); *A61K 47/48238* (2013.01); *A61K 47/48323* (2013.01); *A61K 47/48338* (2013.01); *A61K 47/48815* (2013.01); *A61K 47/48853* (2013.01); *Y10S 977/80* (2013.01); *Y10S 977/801* (2013.01); *Y10S 977/907* (2013.01)

(56) References Cited

U.S. PATENT DOCUMENTS

| | | | |
|---|---|---|---|
| 2006/0210549 | A1 | 9/2006 | Srivastava et al. |
| 2007/0041904 | A1 | 2/2007 | Jiang et al. |
| 2008/0213377 | A1 | 9/2008 | Agarwal et al. |
| 2009/0016962 | A1 | 1/2009 | Fukumura et al. |
| 2009/0022782 | A1 | 1/2009 | Akita et al. |

FOREIGN PATENT DOCUMENTS

| | | |
|---|---|---|
| WO | WO2006125134 | 11/2006 |
| WO | WO2012155920 | 11/2012 |

OTHER PUBLICATIONS

H Hatakeyama, H Akita, K Kogure, M Oishi, Y Nagasaki, Y Kihira, M Ueno, H Kobayashi, H Kikuchi, H Harashima. "Development of a Novel Systemic Gene Delivery System for Cancer Therapy with a Tumor-Specific Cleavable PEG-lipid." Gene Therapy, vol. 14, 2007, pp. 69-77.*

T Terada, M Iwai, S Kawakami, F Yamashita, M Hashida. "Novel PEG-matrix Metalloproteinase-2 Cleavable Peptide-Lipid Containing Galactosylated Liposomes for Hepatocellular Carcinoma-Selective Targeting." Journal of Controlled Release, vol. 111, 2006, pp. 333-342.*

JH Jang, MY Kim, JW Lee, SC Kim, JH Cho. "Enhancement of the cancer targeting specificity of buforin IIb by fusion with an anionic peptide via a matrix metalloproteinases-cleavable linker." Peptides, vol. 32, 2011, pp. 895-899, available online Feb. 18, 2011.*

MJ Roberts, MD Bentley, JM Harris. "Chemistry for peptide and protein PEGylation." Advanced Drug Delivery Reviews, vol. 54, 2002, pp. 459-476.*

Mok, H., "Enhanced Intracellular Delivery of Quantum Dot and Adenovirus Nanoparticles Triggered by Acidic pH via Surface Charge Reversal," Bioconjugate Chemistry, 2008, vol. 19, No. 4, pp. 797-801.

Aguilera, T. et al, "Systemic in vivo distribution of activatable cell penetrating peptides is superior to that of cell penetrating peptides", Integrative Biology, vol. 1, pp. 371-381, (May 11, 2009).

Bisby, R. et al (1), "Photosensitive liposomes as 'cages' for laser-triggered solute delivery: the effect of bilayer cholesterol on kinetics of solute release", Federation of European Biochemical Societies, FEBS Letters 23043, vol. 463, pp. 165-168, (Nov. 6, 1999).

Bisby, R. et al (2), "Fast laser-induced solute release from liposomes sensitized with photochromic lipid: Effects of temperature, lipid host, and sensitizer concentration", Biochemical and Biophysical Research Communications, vol. 262, pp. 406-410, (Jul. 20, 1999).

Dahr, S. et al, "Mitaplatin, a potent fusion of cisplatin and the orphan drug dichloroacetate", PNAS, 106:52:22199-22204, Internet article: http://www.pnas.org/cgi/doi/10.1073/pnas.091226106, (Dec. 29, 2009).

Gu, J. et al, "pH-triggered reversible 'stealth' polycationic micelles", American Chemical Society, Biomacromolecules, XP-002659924, vol. 9, pp. 255-262, (Sep. 30, 2007).

Hatakeyama, H. et al, "Development of a novel systemic gene delivery system for cancer therapy with a tumor-specific cleavable PEG-lipid", Gene Therapy, vol. 14, pp. 68-77, Internet article: http://nature.com/gt, (2007).

Jolck, R. et al, "Solid-phase synthesis of PEGylated Lipopeptides using click chemistry", Amer. Chem. Soc., Bioconjugate Chemistry, vol. 21, pp. 807-810, (Mar. 29, 2010).

Kumar, V. et al, "On the disulfide-linker strategy for designing efficacious cationic transfection lipids: an unexpected transfection profile", Federation of European Biochemical Societies, FEBS Letters 28609, vol. 571, pp. 205-211, (Jun. 11, 2004).

Mignet, N. et al , "Anionic pH-sensitive peglyated lipoplexes to deliver DNA to tumors", International Journal of Pharmaceuticals, vol. 361, pp. 194-201, (May 17, 2008).

Morgan, C. et al, "Liposome fusion and lipid exchange on ultraviolet irradiation of liposomes containing a photochromic phospholipid", Photochemistry and Photobiology, 62:1:24-29, Feb. 13, 1995).

Olson, E. et al, "In vivo characterization of activatable cell penetrating peptides for targeting protease activity in cancer", Integrative Biology, vol. 1, pp. 382-393, Internet article: http://www.rsc.org/ibiology, (May 11, 2009).

Pak, C. et al (1), "Triggerable liposomal fusion by enzyme cleavage of a novel peptide-lipid conjugate", Biochemica et Biophysica Acta, vol. 1372, pp. 13-27, (Feb. 26, 1998).

Takae, S. et al, "PEG-Detachable polyplex micelles based on disulfide-linked block cationers as bioresponsive nonviral gene vectors", J. Am. Chem. Soc., vol. 130, pp. 6001-6009, XP-002659925, (2008).

Terada, T. et al, "Novel PEG-matrix metalloproteinase-2 cleavable peptide-lipid containing galactosylated liposomes for hepatocellular carcinoma-selective targeting", Journal of Controlled Release, vol. 111, pp. 333-342, (Feb. 20, 2006).

Turk, B. et al, "Determination of protease cleavage site motifs using mixture-based oriented peptide libraries", Internet article: http://biotech.nature.com, vol. 19, pp. 661-667, (Jul. 2001).

Zhang, X. et al, "Synthesis, characterization, and in vitro transfection activity of charge-reversal amphiphiles for DNA delivery", Bioconjugate Chemistry, vol. 27, pp. 690-699, XP-002659811, (2011).

Pak, C. et al, "Elastase activated liposomal delivery to nucleated cells", Biochemica et Biophysica Acta, vol. 1419, pp. 111-126, (1999).

* cited by examiner

CHARGE TRIGGERING OF SELF-ORGANIZED NANOPARTICLES

CROSS-REFERENCE TO RELATED APPLICATIONS

This application is a §371 national stage entry of International Application No. PCT/DK2012/050174, filed May 16, 2012, which claims priority to U.S. Provisional Patent Application No. 61/486,420 filed May 16, 2011, European Patent Application No. 11166163.3 filed May 16, 2011 and European Patent Application No. 12159792.6 as filed Mar. 16, 2012, the entire contents of which are incorporated herein by reference.

FIELD OF THE INVENTION

The present invention relates to novel self-organized nanoparticles useful as drug delivery systems.

BACKGROUND OF THE INVENTION

Treatment of severe diseases such as cancer and arthritis is one of the fundamental challenges in medical research and the search for new drug delivery technologies in this area is intense and is of great interest to all major pharmaceutical companies worldwide.

US 2009/0022782 A1 discloses a blood retainable device exhibiting selective degradability in tumor tissue. The reference discloses compounds consisting of a phospholipid moiety linked to a poly(alkylene glycol) via a linker, which is cleavable by means of a matrix metalloprotease.

US 2007/0041904 A1 discloses peptides including A-X-B-C, where C is a cargo moiety (e.g. a contrast agent for diagnostic imaging, a chemotherapeutic drug, or a radiation-sensitizer), the B portion includes basic amino acids, X is a cleavable linker sequence and the A portion includes acidic amino acids. This A-X-B-C type of compound includes both basic- and acidic amino acids within the same molecule covalently linked through the cleavable linker X.

US 2006/0210549 A1 discloses lipopeptides including A-(B)-C, where A is a fatty acid (e.g. stearic acid), B is a photo labile linker and C is a polypeptide which is cleavable by proteases such as gelatinases and collagenases.

WO 93/04673 discloses the use of vinyl ether phospholipids, which readily are hydrolyzed by reactive oxygen species or acid, to obtain triggered release from liposomal formulations.

Jølck et al. (Bioconjugate Chem. (2010) 21, 807-810) discloses an efficient method to synthesize PEGylated lipopeptides with the overall structure A-B-C on solid phase support using Click Chemistry where A is a diacyl fatty acid (e.g. stearic acid, palmitic acid or myristic acid), B is a peptide linker which is cleavable by proteases such as gelatinases and collagenases and C is a polymer such as PEG.

Aguilera et al. (Integr. Biol. (2009) 1, 371-381) disclose the in vivo tissue distribution of protease cleavable peptides A-X-B-C where the A portion includes acidic amino acids, the B portion includes basic amino acids, X is a cleavable linker sequence and C is a fluorescent probe. Both basic- and acidic amino acids are combined in the same molecule covalently linked through the cleavable linker X.

Olson et al. (Integr. Biol. (2009) 1, 382-393) disclose the in vivo tumor uptake and the mechanism of activation of protease cleavable peptides A-X-B-C where the A portion includes acidic amino acids, the B portion includes basic amino acids, X is a cleavable linker sequence and C is a fluorescent probe. Both basic- and acidic amino acids are combined in the same molecule covalently linked through the cleavable linker X.

Mignet et al. (Int. J. Pharmaceutics (2008) 361, 194-201) disclose anionic pH-sensitive PEGylated lipoplexes to deliver DNA to tumors.

Hatakeyama et al. (Gene Therapy (2007) 14, 68-77) disclose a systemic gene delivery system for cancer therapy with a tumor-specific cleavable PEG-lipid.

Terada et al. (J. Controlled Release 111 (2006) 333-342) disclose a study of PEG-matrix metalloprotease-2 cleavable peptide-lipid containing galactosylated liposomes for hepatocellular carcinoma-selective targeting.

Zhang et al. (Bioconjugate Chem. 2011, 22, 690-699) disclose amphiphile for DNA delivery.

Mok et al. (Bioconjugate Chem. 2008, 19, 797-801) disclose poly(L-lysine) grafted with multiple biotin-PEG chains.

Gu et al. (Biomacromolecules 2008, 9, 255-262) disclose amphiphile polycations.

Takae et al. (J. Am. Chem. Soc. 2008, 130, 6001-6009) disclose disulfide-linked block catiomers.

Pak et al. (Biochimica et Biophysica Acta 1419 (1999) 111-126) discloses activation of liposomes for delivery.

WO 2006/125134 A1 discloses peptides of the generic structure A-X-B-C where A includes acidic amino acids, X is a cleavable linker, B includes basic amino acids, and C is a cargo moiety.

The present invention offers a solution to one of the fundamental problems in developing nanoparticle-based drug delivery systems for intravenous administration of drugs, which is the route of choice in cancer treatment, i.e. to activate drug release specifically at or in the diseased tissue while maintaining high stability during blood circulation.

SUMMARY OF THE INVENTION

It has been found by the present inventor(s) that it is possible to trigger a change in the surface charge, and thereby the surface accessibility of self-organized nanoparticles specifically in diseased tissue by utilizing a new class of organic moieties (e.g. lipid or polymer based), with irreplaceable properties.

So, in a first aspect the present invention relates to triggering a change in surface charge of self-organized nanoparticles containing neutral and positive charged lipid moieties in addition to a molecule of the formula A-B-C(-D) (A designates an anchoring moiety having self-organizing properties, B designates a cleavable linker, e.g. a linker which is cleavable in mammalian tissue, C designates an anionic moiety having a net charge of at least −2 at pH 6.0, and D (optional) designates a polymer moiety which induces long circulating properties of the nanoparticle in mammalian tissue) by cleavage of the linker B caused by biological activation (e.g. enzymatic cleavage, hydrolysis, reduction, oxidation etc.) or external stimuli such as e.g. electromagnetic radiation e.g. UV-radiation, into A-B' and B"-C-(D) fragments.

A second aspect of the present invention relates to fine tuning of the self-organized nanoparticles by chemical separation of the anionic- and cationic charges. This non-covalent association between the anionic- and cationic charges enables rapid fine tuning of the system resulting in full control surface charge of the self-organized nanoparticles (see, e.g. FIG. 7).

A third aspect of the present invention relates to triggering drug release in the tissue of interest. In situ activation of the self-organized nanoparticles by cleavage of the linker B resulting in release of the large B"-C(-D) fragment introduces a substantial reorganization of the self-organized nanoparticle resulting in drug release in the tissue of interest e.g. tumor and/or inflammatory tissue.

A fourth aspect of the present invention relates to in vivo transfection in the tissue of interest. Cleavage of the linker B resulting in release of the large B"-C(-D) fragment thereby introducing a positive charge specifically at the diseased target site utilizes what is already known in the gene transfection systems and are readily internalized by cells, however, they are not utilizable for in vivo application due to unspecific and toxic side-effects as a consequence of the positive charge. By the present invention, this problem is solved because the change in overall surface charge as a consequence of site-specific activation thus enables in vivo gene therapy.

A fifth aspect of the present invention relates to triggering uptake of inorganic colloids in the tissue of interest. In situ activation of monolayer/bilayer coated inorganic colloids by cleavage of the linker B and thereby introducing a positive charge specifically at the diseased target site enables rapid uptake into cells.

A sixth aspect of the present invention relates to introduction of a targeting molecule E (e.g. antibodies, antibody fragments, peptides, vitamins, aptamers etc.) at any position within the molecule A-B-C-(D) e.g. A-E-B-C(-D), A-B-E-C(-D), A-B-C-E(-D) or A-B-C(-D)-E or on a polymer modified anchor exposing the targeting ligand at the distal end of the polymer thereby allowing enhanced accumulation in the diseased tissue or altered pharmacokinetics where the nanoparticles accumulate faster and/or to a higher extend in the diseased tissue.

DETAILED DISCLOSURE OF THE INVENTION

Figure 1:
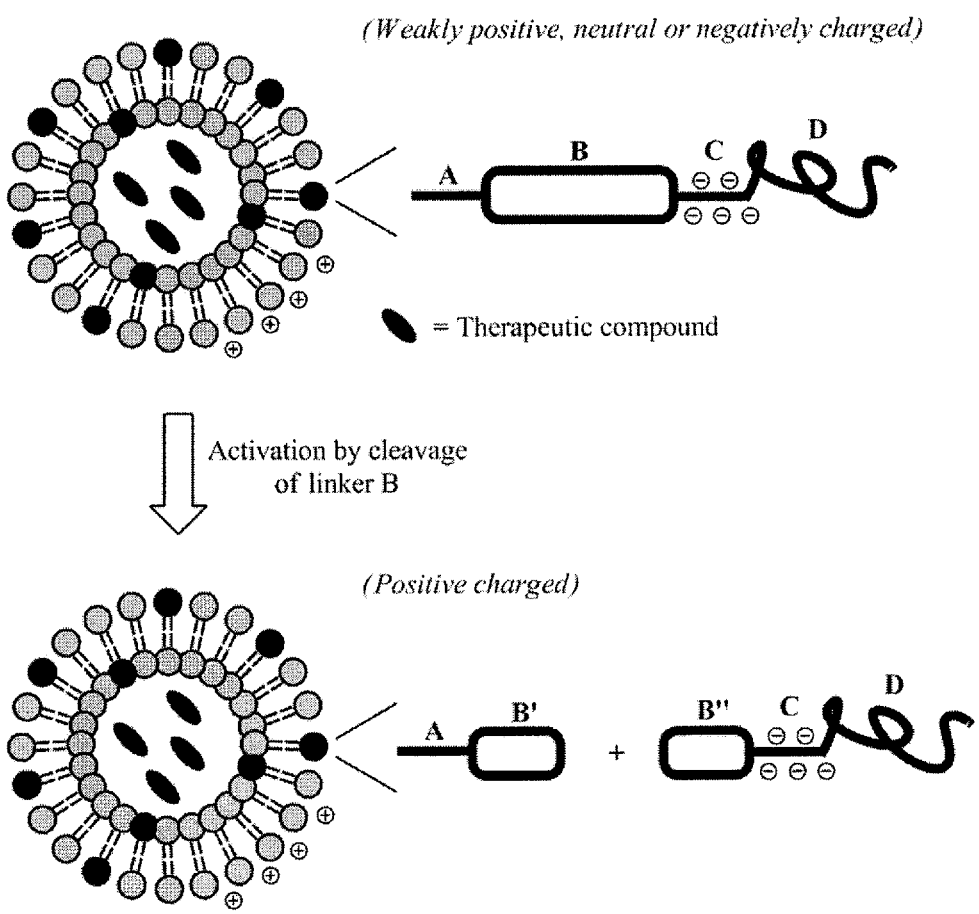
FIG. 1 illustrates a nanoparticle according to the invention in the form of a liposome wherein, e.g., a drug can be encapsulated. The compound A-B-C(-D) is included in the surface of the nanoparticles. The liposome (nanoparticle) is furthermore composed of lipids that are typically positively charged. Due to the negatively charged anionic moiety C of the compound, the overall charge of the liposome (may be evaluated by the surface potential) is weakly positive, neutral, weakly negative or even negative. When the system is activated in the diseased tissue, e.g. by enzyme activation, the anionic moiety, C, is cleaved off by cleavage of the linker B, and the liposome (now only including the anchoring moiety A and any residual of the linker B') becomes positively charged, due to the fact that the negatively charged moiety C is cleaved off. This makes it possible for the liposome to interact e.g. with cancer cells in diseased tissue (cancer cell membranes are negatively charged), and depending on the drug, a range of release mechanisms can be incorporated into the system. Cleaving off the relatively large B"-C(-D) fragment will make it possible to introduce a substantial reorganization of the self-organized nanoparticle allowing drug release. The introduction of positive charge specifically at the diseased target site furthermore utilizes what is already known in the gene transfection systems and are readily internalized by cells; however, they are not utilizable for in vivo application due to unspecific and toxic side-effects as a consequence of the positive charge. By the present invention, this problem is solved because the change in overall surface charge as a consequence of site-specific activation has been proven, also showing that this induces specific interactions with cancer cells.
Figure 2:
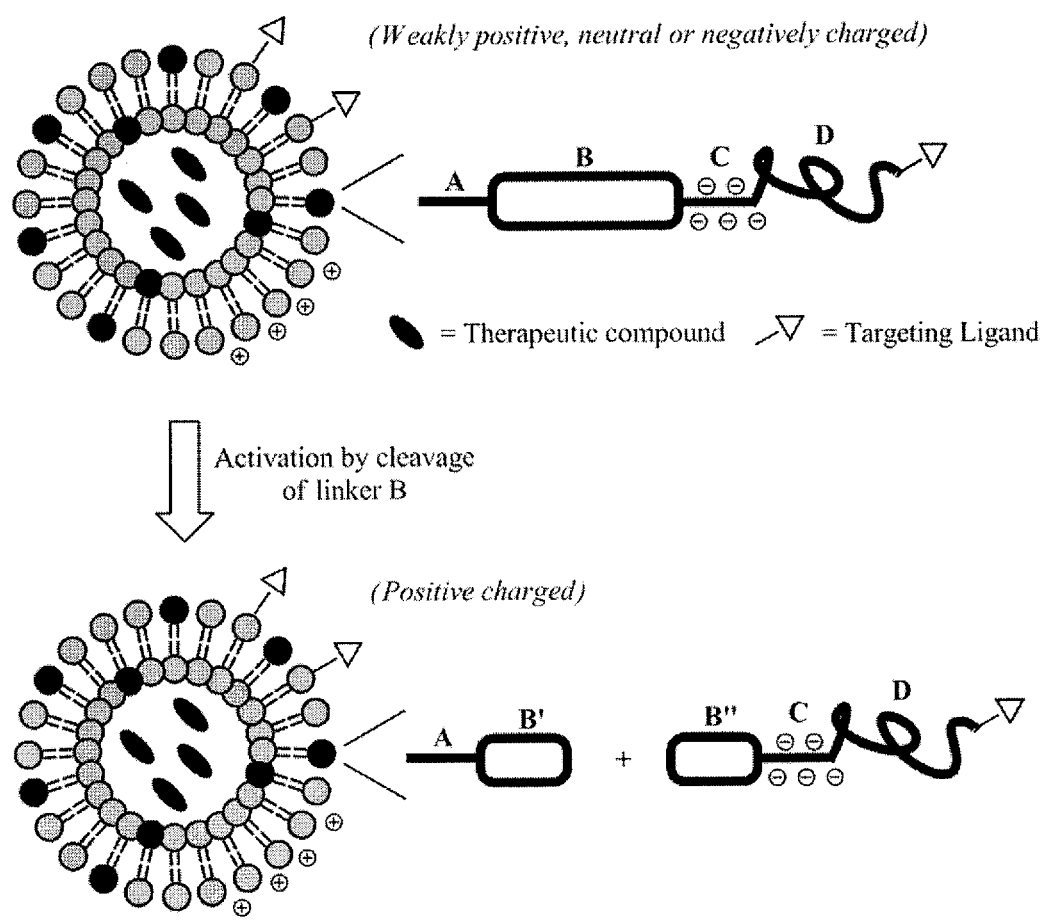
FIG. 2 illustrates the nanoparticle of FIG. 1, but further functionalized with targeting ligands either as a part of the A-B-C(-D) molecule or embedded in the lipid bilayer (or a combination of the two) through hydrophobic-PEG anchors.
Figure 3:
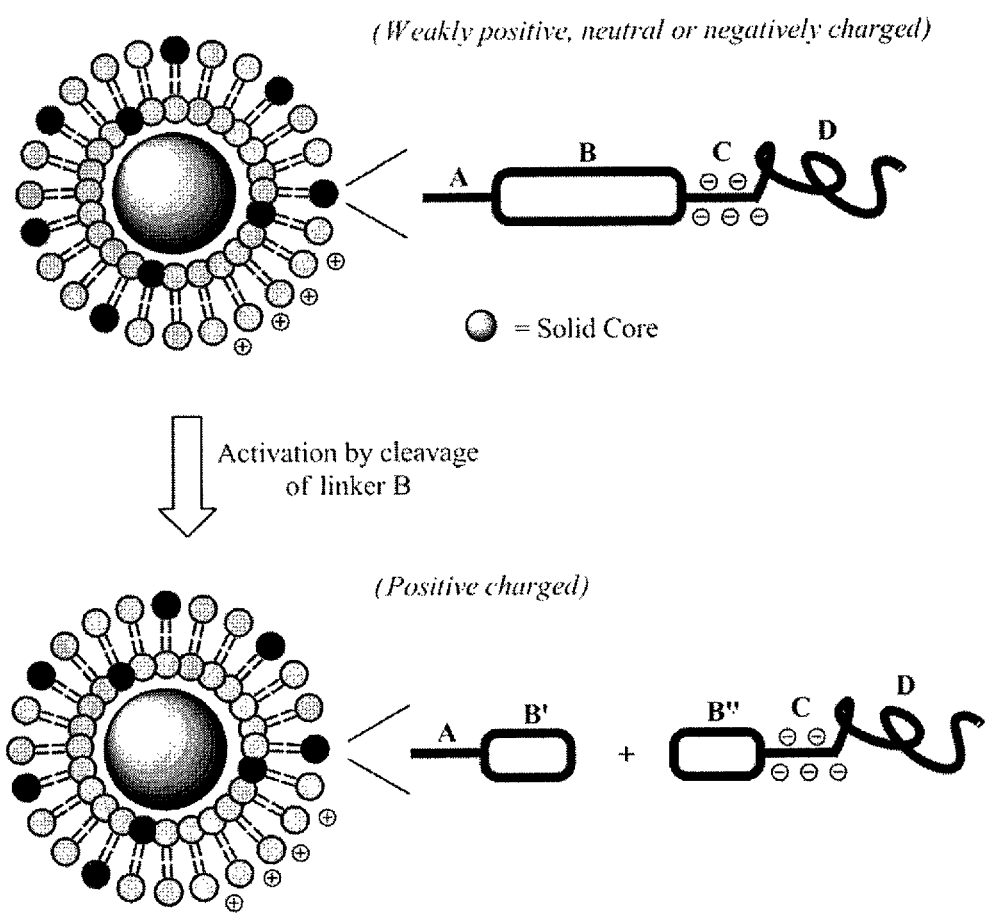
FIG. 3 illustrates a nanoparticle according to the invention in the form of a lipid bilayer stabilized solid colloid. The compound A-B-C(-D) covers the surface of the nanoparticle and it is also possible to add receptor targeting moieties. The lipid bilayer is furthermore composed of lipids that are positively charged. Due to the negatively charged anionic moiety C of the compound, the overall charge of the lipid bilayer (may be evaluated by the surface potential) is weakly positive, neutral, weakly negative or even negative. When the system is activated in the diseased tissue, e.g. by enzyme activation, the anionic moiety is cleaved off by cleavage of the linker B, and the lipid surface (now only including the anchoring moiety A and any residual of the linker B') becomes positively charged. This makes it possible for the lipid coated solid colloid to interact with cancer cells in the diseased tissue (cancer cell membranes are negatively charged). The introduction of positive charge specifically at the diseased target site furthermore utilizes what is already known in the gene transfection systems and are readily internalized by cells, however, they are not utilizable for in vivo application due to unspecific and toxic side-effects as a consequence of the positive charge. By the present invention, this problem is solved because the change in overall surface charge as a consequence of site-specific activation has been proven, also showing that this induces specific interactions with cancer cells.
Figure 4:
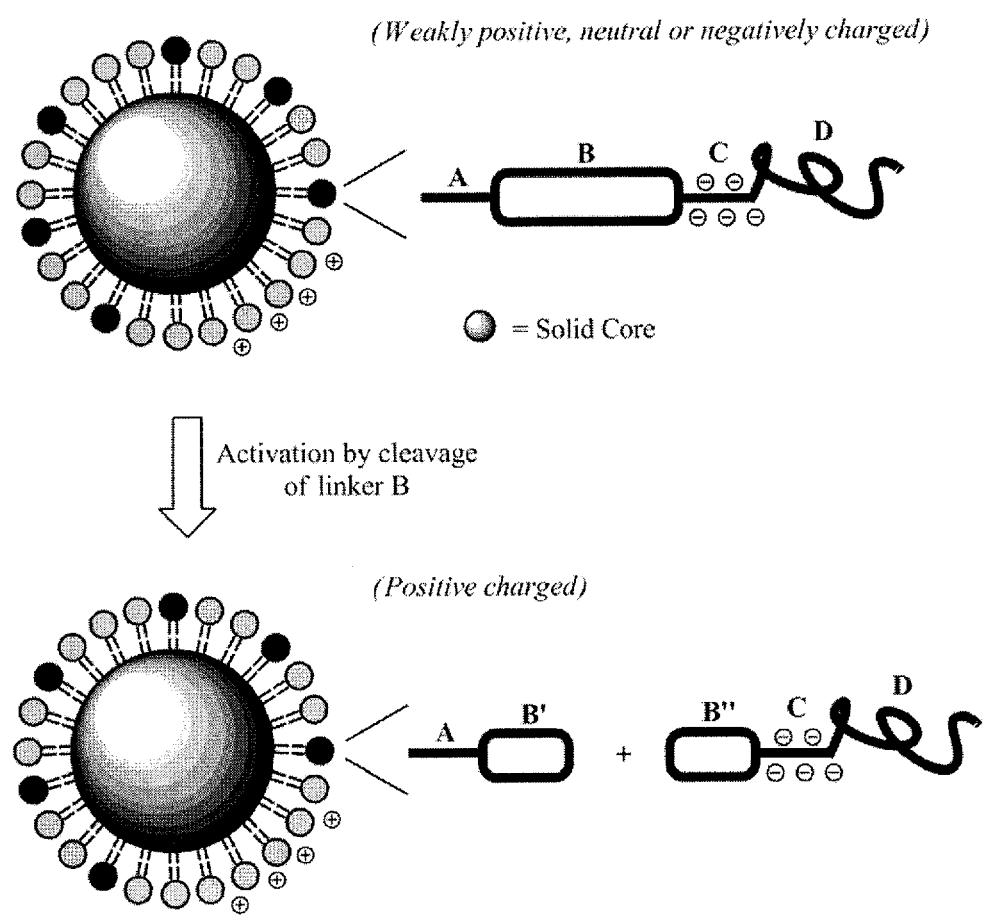
FIG. 4 illustrates a nanoparticle according to the invention in the form of a lipid monolayer stabilized solid colloid with a hydrophobic surface. The compound A-B-C(-D) covers the surface of the nanoparticle and it is also possible to add receptor targeting moieties. The lipid monolayer is furthermore composed of lipids that are positively charged. Due to the negatively charged anionic moiety C of the compound, the overall charge of the lipid monolayer (may be evaluated by the surface potential) is weakly positive, neutral, weakly negative or even negative. When the system is activated in the diseased tissue, e.g. by enzyme activation, the anionic moiety is cleaved off by cleavage of the linker B, and the lipid surface (now only including the anchoring moiety A and any residual of the linker B') becomes positively charged. This makes it possible for the lipid coated solid colloid to interact with cancer cells in the diseased tissue (cancer cell membranes are negatively charged). The introduction of positive charge specifically at the diseased target site furthermore utilizes what is already known in the gene transfection systems and are readily internalized by cells, however, they are not utilizable for in vivo application due to unspecific and toxic side-effects as a consequence of the positive charge. By the present invention, this problem is solved because the change in overall surface charge as a consequence of site-specific activation has been proven, also showing that this induces specific interactions with cancer cells.

The present invention i.a. relates to self-organized nanoparticles comprising as a part of its surface structure a plurality of compounds of the formula A-B-C(-D). The compounds of the formula A-B-C(-D) include the anionic moiety C, which changes the overall charge of the nanoparticle. The nanoparticles including compound of the formula A-B-C(-D) will have long-circulating properties and will tend to accumulate in diseased tissue upon intravenous administration, e.g. in cancerous tissue due to the high endothelium permeability and low lymphatic drainage, known as the enhanced permeation and retention (EPR) effect. When pharmaceutically active agent(s) and/or diagnostically relevant species are included in the nanoparticle (see further below), the nanoparticle can release this agent(s)/species specifically in diseased tissue due to cleavage of the linker B as a response to the biological activation and/or external stimuli.

Self-Organized Nanoparticles

One aspect of the present invention is a self-organized nanoparticle comprising as a constituent thereof a plurality of compounds of the formula A-B-C(-D), wherein;

A designates an anchoring moiety having self-organizing properties in relation to the nanoparticle;

B designates a cleavable linker;

C designates an anionic moiety having a net charge of at least −2 at pH 6.0; and D, which is optional, designates a polymer moiety which induces long circulating properties of the nanoparticle in mammalian tissue;

and wherein the overall net charge of the compounds is at least −1 at pH 6.0.

In the present context, the term "nanoparticle" is intended to mean a particulate structure having a diameter in the sub-micrometer range, i.e. a diameter of less than 1,000 nm, typically in the range of 1 to 500 nm. Illustrative examples of relevant nanoparticle structures within the present context are micelles, liposomes (including unilamella liposomes and multi-lamella liposomes), polymersomes, lipoplexes, polyplexes and polymer films.

In the present context, the term "solid colloid" is intended to mean a particulate structure having a diameter in the sub-micrometer range, i.e. a diameter of less than 1,000 nm, typically in the range of 1 to 500 nm. Illustrative examples of relevant solid colloids are any ferrite or mixed ferrite materials, preferably of a uniform, controllable size and narrow size distribution, wherein the primary component, the oxide, is of the formula $M_2^{(+3)}M^{(+2)}O_4$, wherein $M^{(+3)}$ is Al, Cr or Fe, and $M^{(+2)}$ is Fe, Ni, Co, Zn, Zr, Sr, Ca, Ba, Mg, Ga, Gd, Mn or Cd, and the oxides can be mixed with LiO, CdO, NiO, FeO, ZnO, NaO, KO and mixtures thereof. Solid colloids can also comprise a solid inorganic core consisting of metals and metal oxides of Au, Fe, Co, Ni, Zn, Mn, Mg, Ca, Ba, Sr, Cd, Hg, Al, B, Sc, Ga, V, In, and mixtures thereof.

In the present context, the term "self-organized" is intended to mean a process where the materials spontaneously forms a supramolecular aggregates due to e.g. hydrophobic effects, hydrophilic effects, electrostatic interactions, ionic interactions, van der Waals forces, pi-pi interactions, peptide/protein folding, hydrogen bonding, and combinations thereof.

Examples of compounds which are capable of forming self-organized nanoparticles are—in addition to the compounds of the invention—surfactant molecules, e.g. phospholipids, monoglycerides, diglycerides, triglycerides, sterols, fatty acids, sphingolipids, lipid-saccharides, ceramides, bola lipids, branched and linear polymers, block copolymers, peptides, lipopeptides and mixtures thereof.

In one embodiment, the self-organized nanoparticle (e.g. a liposome or micelle) has a lipid membrane structure for example phospholipids. The lipid membrane may in addition to the compounds of the invention and any phospholipids include one or more of a sterol such as cholesterol, and cholestanol, a fatty acid having a saturated or unsaturated acyl group having 8 to 22 carbon atoms and an antioxidant such as alpha-tocopherol. Examples of the phospholipids include, for example, phosphatidylethanolamines, phosphatidylcholines, phosphatidylserines, phosphatidylinositols, phosphatidylglycerols, cardiolipins, sphingomyelins, ceramide phosphorylethanolamines, ceramide phosphorylglycerols, ceramide phosphorylglycerol phosphates, 1,2-dimyristoyl-1,2-deoxy-phosphatidylcholines, plasmalogens, phosphatidic acids, and the like, and these may be used alone or two or more kind of them can be used in combination. The fatty acid residues of these phospholipids are not particularly limited, and examples thereof include a saturated or unsaturated fatty acid residue having 12 to 20 carbon atoms. Specific examples include an acyl group derived from a fatty acid such as lauric acid, myristic acid, palmitic acid, stearic acid, oleic acid and linoleic acid. Further, phospholipids derived from natural products such as egg yolk lecithin and soybean lecithin can also be used for the preparation of the lipid membrane structure of the present invention. Also usable are, for example, 1,2-bis(oleoyloxy)-3-(trimethylammonio)-propane (DOTAP), 1-N,N-dimethylaminodioleoylpropane (DODAP), 1-oleoyl-2-hydroxy-3-N,N-dimethylaminopropane, 1,2-diacyl-3-N,N-dimethylaminopropane, 1,2-didecanoyl-1-N,N-dimethylaminopropane, 3-beta-[n-[(N',N'-dimethylamino)ethane]carbamoyl]cholesterol (DC-Chol), 1,2-dimyristyloxypropyl-3-dimethylhydroxyethylammonium bromide (DMRIE), 1,2-dioleoyloxypropyl-3-dimethylhydroxyethylammonium bromide (DORI), and the like.

A lipid derivative having, for example, function for imparting retainability in blood, temperature change-sensitivity, pH-sensitivity, UV-sensitivity, redox sensitivity or the like may be contained in the lipid membrane of the nanoparticle structure as a membrane component lipid, one or more of these functions can be thereby imparted, and by imparting one or more of these functions, for example, blood retainability of the lipid membrane structure containing a medicament and/or a gene can be improved, a rate of capture by reticuloendothelial systems of liver, spleen and the like can be reduced, or a releasing property of the medicament and/or gene can be enhanced. Examples of lipid derivatives retainable in blood, which can impart the function for imparting retainability in blood, include, for example, glycophorin, ganglioside GM1, phosphatidylinositol, ganglioside GM3, glucuronic acid derivative, glutamic acid derivative, polyglycerin-phospholipid derivative, polyethylene glycol derivatives such as N-{carbonyl-methoxypolyethylene glycol-2000}-1,2-dipalmitoyl-sn-glycero-3-phosphoethanolamine, N-{carbonyl-methoxypolyethylene glycol-5000}-1,2-dipalmitoyl-sn-glycero-3-phosphoethanolamine, N-{carbonyl-methoxypolyethylene glycol-750}-1,2-distearoyl-sn-glycero-3-phosphoethanolamine, N-{carbonyl-methoxypolyethylene glycol-2000}-1,2-distearoyl-sn-glycero-3-phosphoethanolamine and N-{carbonyl-methoxypolyethylene glycol-5000}-1,2-distearoyl-sn-glycero-3-phosphoethanolamine, and the like. Examples of temperature change-sensitive lipid derivatives that can impart the temperature change-sensitive function include, for example, dipalmitoylphosphatidylcholine and the like. Examples of pH-sensitive lipid derivatives that can impart the pH-sensitive function include, for example, dioleoylphosphatidylethanolamine and the like. Examples of UV-sensitive lipid derivatives that can impart the UV-sensitive function include, for example, bis-azo phosphatidylcholine and the like, see, e.g., (a) Morgan et al. Photochem. Photobiol. (1995) 62, 24-29, b) Bisby et al. FEBS Lett. (1999) 463, 165-168 and c) Bisby et al. Biochem. Biophys. Res. Commun. (1999) 262, 406-410). Examples of redox-sensitive lipid derivatives that can impart the redox-sensitive function include, for example, disulfide modified lipids see FEBS Letters, 571, pp. 205-211, 2004.

It is known from the literature, that such self-organized nanoparticles may be useful as drug delivery systems.

The overall net negative charge of the compounds is at least −1 at pH 6.0, such as a negative net charge of at least −1, such as at least −2, or at least −3, or at least −4, such as from −1 to −10, or from −2 to −8.

The Anchoring Moiety

One essential feature of the compound of the formula A-B-C(-D) is the anchoring moiety A. This moiety anchors the compound in the nanoparticle structure, i.e. the moiety A has in itself (even when the linker B is cleaved) self-organizing properties in relation to the nanoparticle in question so that molecules of the compound in combination with other constituents (e.g. phospholipids, etc.) form the self-organized nanoparticle.

Typically, the anchoring moiety A is selected from hydrophobic lipid moieties such as saturated and unsaturated alkyl chains, fatty acids, phospholipids, lysolipids, sterols, ceramides, nano-rods and the like. The anchoring moiety A can be composed of a single or multiply copies of the above listed moieties or as well as mixtures thereof.

In another embodiment, the anchoring moiety A is a hydrophobic or semi-hydrophobic polymer e.g. polystyrene (PS), poly(methyl methacrylate) (PMMA), polyphenylene oxide (PPO), polycaprolactone (PCL) and the like or any copolymer/block copolymer including the before mentioned polymers.

In one interesting embodiment, the anchoring moiety is a residue of a phospholipid. As the phospholipid, phosphatidylethanolamines, phosphatidylcholines, phosphatidylserines, phosphatidylinositols, phosphatidylglycerols, cardiolipins, sphingomyelins, ceramide phosphorylethanolamines, ceramide phosphorylglycerols, ceramide phosphorylglycerol phosphates, 1,2-dimyristoyl-1,2-deoxyphosphatidylcholines, plasmalogens and phosphatidic acids can be used, and the aliphatic acid residue in these phospholipids is not particularly limited. For example, a phospholipid having one or two saturated or unsaturated aliphatic acid residues each having about 12 to 20 carbon atoms can be used, and specifically, a phospholipid having one or two acyl groups derived from an aliphatic acid such as lauric acid, myristic acid, palmitic acid, stearic acid, oleic acid, and linoleic acid can be used. Among those mentioned above, phosphatidylethanolamines may be preferred, e.g. dioleoylphosphatidylethanolamine (DOPE). The residue of a phospholipid means a group obtained by eliminating an appropriate atom such as hydrogen atom, or an appropriate functional group such as hydroxyl group or a halogen atom from any of the before mentioned phospholipid or a chemically modified phospholipid, preferably such a monovalent group. Examples include, for example, a residue obtained by eliminating hydrogen atom from hydroxyl group of phosphoric acid moiety of a phospholipid, a residue obtained by eliminating hydroxyl group of phosphoric acid moiety of a phospholipid, a residue obtained by eliminating hydrogen atom binding to a carbon atom of a phospholipid, a residue obtained by introducing a functional group comprising carboxyl group into phosphoric acid moiety of a phospholipid and eliminating hydroxyl group or hydrogen atom from the carboxyl group, and the like.

With respect to the charge contribution of the anchoring moiety, it is typically rather insignificant. Hence, in some interesting embodiments, the net charge of the anchoring moiety is close to neutral, such as from −2 to +2, or from −2 to +1, or from −1 to +2, such as from −1 to +1, or from −2 to 0.

Hence, when turning to the remaining portion of the compound, namely B-C(-D), the overall net negative charge of that portion is typically at least −1 at pH 6.0, such as a negative net charge of at least −1, such as at least −2, or at least −3, or at least −4, such as from −1 to −10, or from −2 to −8.

When referred to herein, the expressions "average net charge", "charge" and "net charge" refers to the charge at pH 6.0. The charge can either be determined based on the knowledge of the functional groups in question (acid groups, amino groups, etc.), or can be determined experimentally as outlined in the Examples section.

The Linker

The cleavable linker B allows for cleavage of the compound so that the anchoring moiety (and possible a residue of the linker B (i.e. B'); commonly designated A-B') can be covalently detached from the remaining part of the compound (B"-C(-D) in mammalian tissue, in particular in diseased tissue. The cleavage of the linker B of the compound may be caused by biological activation within the relevant tissue or, alternatively, by external stimuli such as, e.g., electromagnetic radiation e.g. UV-radiation.

In some interesting embodiments, the part of the compound which is covalently cleaved off, i.e. B"-C(-D), preferably have a negative net charge of at least −1, such as at least −2, or at least −3, or at least −4, such as from −1 to −10, or from −2 to −8.

In one embodiment, the cleavable linker B is configured for cleavage exterior to a cell, e.g. to be cleaved in conditions associated with cell or tissue damage or disease. Such conditions include, for example, acidosis; the presence of intracellular enzymes (that are normally confined within cells), including necrotic conditions (e.g., cleaved by calpains or other proteases that spill out of necrotic cells); hypoxic conditions such as a reducing environment; thrombosis (e.g., a linker B may be cleavable by thrombin or by another enzyme associated with the blood clotting cascade); immune system activation (e.g., a linker B may be cleavable by action of an activated complement protein); or other condition associated with disease or injury.

Figure 5:
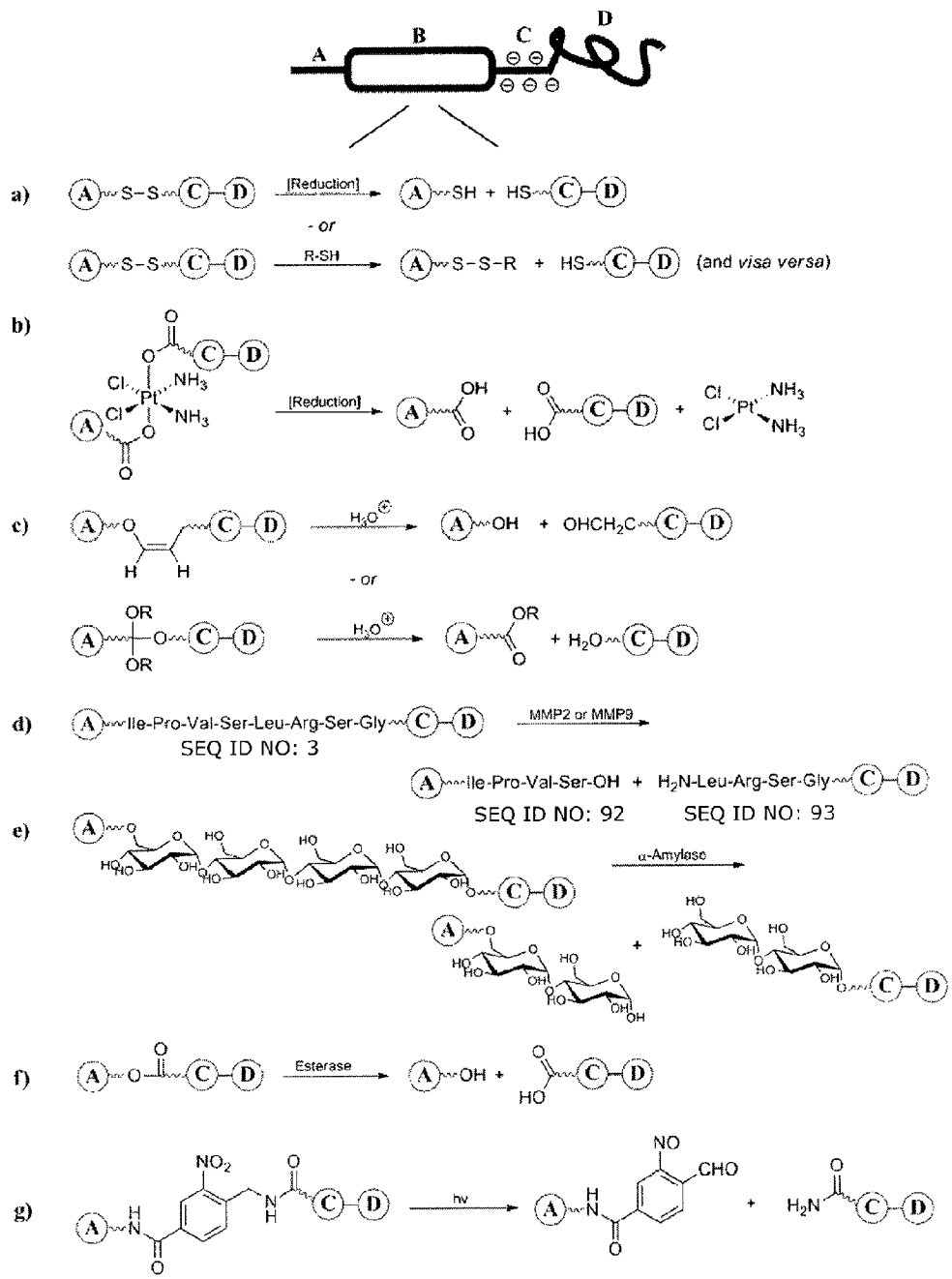
FIG. 5 illustrates a wide range of linkers that the cleavable linker B in the overall structure A-B-C(-D) may be composed of or may include.

In one embodiment, a cleavable linker B may include an S-S linkage (FIG. 5a), or may include a transition metal complex that falls apart when the metal is reduced (FIG. 5b). Illustrative examples of suitable linkers in this respect are the use of Pt(IV) compounds such as Mitaplatin which once exposed to a reductive environment falls apart and reduces to cisplatin and two dichloroacetate molecules (PNAS, 106, pp. 22199-22204, 2009).

Another example pH sensitive linkers which are cleaved upon a change in pH, e.g. at low pH, which will facilitate hydrolysis of acid (or base) labile moieties, e.g. acid labile ester groups etc. Such conditions may be found in the extracellular environment, such as acidic conditions which may be found near cancerous cells and tissues or a reducing environment, as may be found near hypoxic or ischemic cells and tissues; by proteases or other enzymes found on the surface of cells or released near cells having a condition to be treated, such as diseased, apoptotic or necrotic cells and tissues; or by other conditions or factors. An acid-labile linker may be, for example, a cis-aconitic acid linker. Other examples of pH-sensitive linkages include acetals, ketals, activated amides such as amides of 2,3 dimethylmaleamic acid, vinyl ether, other activated ethers and esters such as enol or silyl ethers or esters, imines, iminiums, enamines, carbamates, hydrazones, and other linkages (FIG. 5c). The expression "pH sensitive" refers to the fact that the cleavable linker in question is substantially cleaved at an acidic pH (i.e. a pH below 6.0, such as in the range of 4.0-6.0.

In still another embodiment, the cleavable linker B is configured for cleavage by an enzyme, such as a protease (e.g. pepsin, trypsin, thermolysine or matrix metalloprotease (MMP)) (FIG. 5d), a glycosidase (e.g. α-, β-, γ-amylase, α-, β-glucosidase or lactase) (FIG. 5e) or an esterase (e.g. acetyl cholinesterase, pseudo cholinesterase or acetyl esterase) (FIG. 5f). Other enzymes which may cleave the cleavable linker include urokinase plasminogen activator (uPA), lysosomal enzymes, cathepsins, prostate-specific antigen, Herpes simplex virus protease, cytomegalovirus protease, thrombin, caspase, and interleukin 1 beta converting enzyme.

Still another example is over-expression of an enzyme, e.g. of proteases (e.g. pepsin, trypsin), in the tissue of interest, whereby a specifically designed peptide linker will be cleaved in upon arrival at the tissue of interest. Illustrative examples of suitable linkers in this respect are Gly-Phe-Ser-Gly (SEQ ID NO: 86), Gly-Lys-Val-Ser (SEQ ID NO: 87), Gly-Trp-Ile-Gly (SEQ ID NO: 88), Gly-Lys-Lys-Trp (SEQ ID NO: 89), Gly-Ala-Tyr-Met (SEQ ID NO: 90). It has for example been shown in Example 1, that liposomes exposing RJ111 molecules with the peptide linker Trp-Ile-Pro-Val-Ser-Leu-Arg-Ser-Gly (SEQ ID NO: 80) efficiently was cleaved by addition of Thermolysine.

In still another example, over-expression of an enzyme, e.g. of glycosidases (e.g. α-amylase), in the tissue of interest, causes a specifically designed carbohydrate linker to be cleaved upon arrival at the tissue of interest. Illustrative examples of suitable linkers in this respect are -(α-1-4-D-Glucose)$_n$- where n≥4 (FIG. 5e).

In still another example, the cleavable linker B is configured for cleavage by electromagnetic radiation e.g. UV-radiation (FIG. 5f). UV-exposure of the tissue of interest resulting in cleavage of the linker B can facilitate drug release or facilitate nanoparticles uptake in the desired tissue.

The cleavable linker B may include a total of from 2 to 600 atoms, such as from 6 to 180 atoms.

The cleavable linker B may include amino acid residues, and may be a peptide linkage, e.g. of from 1 to 30, or from 2 to 10, amino acid residues. In one variant, the cleavable linker B consists of from 1 to 30, such as from 2 to 10, or from 2 to 8, or from 3 to 9, or from 4-10, amino acids.

For pH sensitive linkers, the number of atoms is typically from 2 to 50, such as from 2-30.

In some embodiments of the invention, the linker B includes an aminocaproic acid (also termed aminohexanoic acid) linkage or a linkage composed of from 1 to 30, or from 2 to 10 carbohydrate residues.

In one currently very interesting embodiment, the linker B includes a peptide, hereinafter designated "B*", that can serve as a substrate of a matrix metalloproteinase. As the matrix metalloproteinase, for example, MMP-1 (interstitial collagenase), MMP-2 (gelatinase A), MMP-3, MMP-7, MMP-9 (gelatinase B), and the like are known, and a substrate peptide that can serve as a substrate of one or more kinds of matrix metalloproteinases among those mentioned above can be used. For matrix metalloproteinases, see for example, "Molecular mechanism of cancer metastasis", Ed. by Tsuruo T., pp. 92-107, Medical View Co., Ltd., published in 1993.

As for the substrate peptide B* that can serve as a substrate of a matrix metalloproteinase, for example, the matrix metalloproteinases of particular types and substrate peptides specifically recognized thereby are explained in Nature Biotechnology, 19, pp. 661-667, 2001. Therefore, by referring to this publication, a substrate peptide specifically cleaved by a particular type of matrix metalloproteinase can be chosen. For example, Val-Pro-Leu-Ser-Leu-Tyr-Ser-Gly (SEQ ID NO: 91) is known as a specific substrate for MMP-9, and it is preferable to use the aforementioned octapeptide as a substrate peptide that can serve as a substrate of MMP-9.

Illustrative examples of the substrate peptide B* that can serve as a substrate of a matrix metalloproteinase include Gly-Pro-Gln-Gly-Ile-Ala-Gly-Gln (SEQ ID NO: 1), Val-Pro-Met-Ser-Met-Arg-Gly-Gly (SEQ ID NO: 2), Ile-Pro-Val-Ser-Leu-Arg-Ser-Gly (SEQ ID NO: 3), Arg-Pro-Phe-Ser-Met-Ile-Met-Gly (SEQ ID NO: 4), Val-Pro-Leu-Ser-Leu-Thr-Met-Gly (SEQ ID NO: 5), Ile-Pro-Glu-Ser-Leu-Arg-Ala-Gly (SEQ ID NO: 6), Arg-His-Asp, Arg-Pro-Lys-Pro-Val-Glu-Nva-Trp-Arg-Lys (SEQ ID NO: 7), Arg-Pro-Lys-Pro-Tyr-Ala-Nva-Trp-Met-Lys (SEQ ID NO: 8), Pro-Gln-Gly-Ile-Ala-Gly-Gln-Arg (SEQ ID NO: 9), Pro-Leu-Gly-Ile-Ala-Gly-Arg (SEQ ID NO: 10), Gly-Pro-Leu-Gly-Pro (SEQ ID NO: 11), Gly-Pro-Leu-Gly-Pro (SEQ ID NO: 12), and the like.

The linker B may, besides the substrate peptide B*, contain connectors, B1 and B2, involved in the bond or bonds with the anchoring moiety A and the anionic moiety C. Such connectors B1 and B2 may each consist of one amino acid residue or of an oligopeptide containing from 2 to 10, such as from 3 to 9, or from 4 to 8, or from 2 to 8, amino acid residues. The amino acid residue or oligopeptide as the connectors may, if present, bind to both ends of the substrate peptide, or may bind only to one end of the substrate peptide so as to represent one of the structures A-B1-B*-B2-C(-D), A-B*-B2-C(-D), A-B1-B*-C(-D), and A-B*-C(-D). Types of one amino acid usable as the connector(s), and amino acid residues constituting an oligopeptide usable as the connector(s) are not particularly limited, and one amino acid residue of an arbitrary type, or an arbitrary oligopeptide containing, e.g., from 2 to 8 of the same or different amino acid residues of arbitrary types can be used. Examples of the oligopeptide usable as the connector(s) include, for example, -Leu-Gly-, -Tyr-Gly-, -Phe-Gly-, -Gly-Phe-Gly-, -Gly-Gly-Phe-Gly- (SEQ ID NO: 13), -Gly-Phe-Gly-Gly- (SEQ ID NO: 14), -Phe-Gly-Gly-Gly- (SEQ ID NO: 15), -Phe-Phe-Gly-Gly-(SEQ ID NO: 16), -Gly-Gly-Gly-Phe-Gly- (SEQ ID NO: 17), -Gly-Gly-Phe-Phe- (SEQ ID NO: -Gly-Gly-Gly-Gly-Gly-Gly- (SEQ ID NO: 19), -Phe-Phe-, -Ala-Gly-, -Pro-Gly-, -Gly-Gly-Gly-Phe- (SEQ ID NO: 20), -Gly-, -D-Phe-Gly-, -Gly-Phe-, -Ser-Gly-, -Gly-Gly-, -Gly-Gly-Gly-, -Gly-Gly-Gly-Gly- (SEQ ID NO: 21), -Gly-Gly-Leu-Gly- (SEQ ID NO: 22), -Gly-Gly-Tyr-Gly- (SEQ ID NO: 23), -Gly-Gly-Val-Leu- (SEQ ID NO: 24), -Gly-Gly-Leu-Leu-(SEQ ID NO: 25), -Gly-Gly-Phe-Leu- (SEQ ID NO: 26), -Gly-Gly-Tyr-Leu- (SEQ ID NO: 27), -Gly-Gly- Val-Gln- (SEQ ID NO: 28), -Gly-Gly-Leu-Gln- (SEQ ID NO: 29), -Gly-Gly-Ile-Gln (SEQ ID NO: 30), -Gly-Gly-Phe-Gln- (SEQ ID NO: 31), -Gly-Gly-Tyr-Gln- (SEQ ID NO: 32), -Gly-Gly-Trp-Gln- (SEQ ID NO: 33), -Gly-Gly-Leu-Ser- (SEQ ID NO: 34), -Gly-Gly-Phe-Ser-(SEQ ID NO: 35), -Gly-Gly-Tyr-Ser- (SEQ ID NO: 36), -Gly-Gly-Val-Thr- (SEQ ID NO: 37), -Gly-Gly-Leu-Thr- (SEQ ID NO: 38), -Gly-Gly-Phe-Thr- (SEQ ID NO: 39), -Gly-Gly-Tyr-Thr-(SEQ ID NO: 40), -Gly-Gly-Trp-Thr- (SEQ ID NO: 41), -Gly-Gly-Val-Met- (SEQ ID NO: 42), -Gly-Gly-Leu-Met- (SEQ ID NO: 43), -Gly-Gly-Ile-Met- (SEQ ID NO: 44), -Gly-Gly-Phe-Met-(SEQ ID NO: 45), -Gly-Gly-Tyr-Met- (SEQ ID NO: 46), -Gly-Gly-Val-Cit- (SEQ ID NO: 47), -Gly-Gly-Leu-Cit- (SEQ ID NO: 48), -Gly-Gly-Phe-Cit- (SEQ ID NO: 49), -Gly-Gly-Tyr-Cit-(SEQ ID NO: 50), -Gly-Gly-Trp-Cit- (SEQ ID NO: 51), -Gly-Gly-Gly-Asn- (SEQ ID NO: 52), -Gly-Gly-Ala-Asn- (SEQ ID NO: 53), -Gly-Gly-Val-Asn- (SEQ ID NO: 54), -Gly-Gly-Leu-Asn-(SEQ ID NO: 55), -Gly-Gly-Ile-Asn- (SEQ ID NO: 56), -Gly-Gly-Gln-Asn- (SEQ ID NO: 57), -Gly-Gly-Thr-Asn- (SEQ ID NO: 58), -Gly-Gly-Phe-Asn- (SEQ ID NO: 59), -Gly-Gly-Tyr-Asn- (SEQ ID NO: 60), -Gly-Gly-Met-Asn- (SEQ ID NO: 61), -Gly-Gly-Pro-Asn- (SEQ ID NO: 62), -Gly-Gly-Cit-Asn- (SEQ ID NO: 63), -Gly-Gly-Trp-Gly- (SEQ ID NO: 64), -Gly-Gly-Ser-Asn-(SEQ ID NO: 65), -Gly-Gly-Pro-Ala- (SEQ ID NO: 66), -Gly-Gly-Pro-Val- (SEQ ID NO: 67), -Gly-Gly-Pro-Leu- (SEQ ID NO: 68), -Gly-Gly-Pro-Ile- (SEQ ID NO: 69), -Gly-Gly-Pro-Gln-(SEQ ID NO: 70), -Gly-Gly-Pro-Ser- (SEQ ID NO: 71), -Gly-Gly-Pro-Tyr- (SEQ ID NO: 72), -Gly-Gly-Pro-Met- (SEQ ID NO: 73), -Gly-Gly-Met-Pro- (SEQ ID NO: 74), -Gly-Gly-Pro-Pro- (SEQ ID NO: 75), -Gly-Gly-Pro-Cit- (SEQ ID NO: 76), -Gly-Gly-Ile-Leu- (SEQ ID NO: 77), -Gly-Gly-Ile-Cit- (SEQ ID NO: 78), and the like. Among them, -Gly-Gly- or -Gly-Gly-Gly- is preferred as the connector(s).

With respect to the charge contribution, it is preferred that the linker has a net charge of at the most +10, such as at the most +8, or at the most +5, or at the most +3, such as at the most +2, in particular at the most +1, e.g. from −3 to +10, or from −2 to +8, or from −1 to +5. In most preferred embodiments, the linker has a net charge of from −1 to +3, such as from −1 to +2. The net charge of the linker is not particularly critical as long as the overall net charge of the compound is within the limits specified.

The Anionic Moiety

The anionic moiety C has a net negative charge of at least −2, such as at least −3, or at least −4, or at least −5, at pH 6.0. Noting that the overall net negative charge of the compound should be at least −1 at pH 6.0, the compound counters positive charges which may originate from other constituents of the nanoparticle structure, such that the overall charge of the nanoparticle will be comparatively less positive than without the inclusion of the compound, or even will be overall neutral or have an overall negative charge. In most embodiments, the net negative charge of the anionic moiety C is from −20 to −2, such as from −12 to −2, or from −10 to −3, or from −8 to −3.

The negative charges are typically provided by means of carboxylic acid groups which are in the anionic form at pH 6.0. In still another embodiment, the negative charges are provided by means of sulfinic-, sulfonic-, phosphinic- or phosphonic acid groups which are in the anionic form at pH 6.0.

In some interesting embodiments, the net charge of the anionic moiety C is at least −3 at pH 6.0, such as from −3 to −30, e.g. from −3 to −25, or from −4 to −20.

The overall net charge of the compound A-B-C(-D) is typically −1 at pH 6.0, such as from −2 to −30, or −2 to −25 or −3 to −20.

Examples of suitable anionic moieties are peptides and peptide derivatives, such as those including glutamic acid, aspartic acid, phosphoserine, γ-hydroxy-glutamic acid, γ-methylene-glutamic acid, γ-carboxy-glutamic acid, α-aminoapidic acid, 2-aminoheptanedioic acid, α-aminosuberic acid and/or 4-carboxy-phenylalanine. If the anionic moiety is a peptide, the individual amino acid building blocks may be L-amino acids, D-amino acids, racemic amino acids, or a mixture of the before-mentioned.

If the anionic moiety C is a peptide or peptide derivative, it typically has multiple acidic amino acids, e.g. from 2 to 20, preferably from 5 to 20 acidic amino acids. Typically, the anionic moiety C has multiple acidic amino acids, e.g. from 2 to 20, or from 3 to 20, or from 4 to 20, or from 5 to 15, preferably from 5 to 9 acidic amino acids. In preferred embodiments, the anionic moiety C comprises 5 to 9 glutamates or aspartates, and may comprise 5 to 9 consecutive glutamates or aspartates or any other acidic amino acid analogues. In total, the anionic moiety C typically comprises a total of from 2 to 25, preferably from 3 to 20, e.g. from 5 to 15, amino acids.

The anionic moiety C can also be negative charged polymers such as hyaluronic acid or heparin. If the anionic moiety C is a polymer, the D component may not be necessary for obtaining long circulation properties of the nanoparticle construct.

Figure 6:
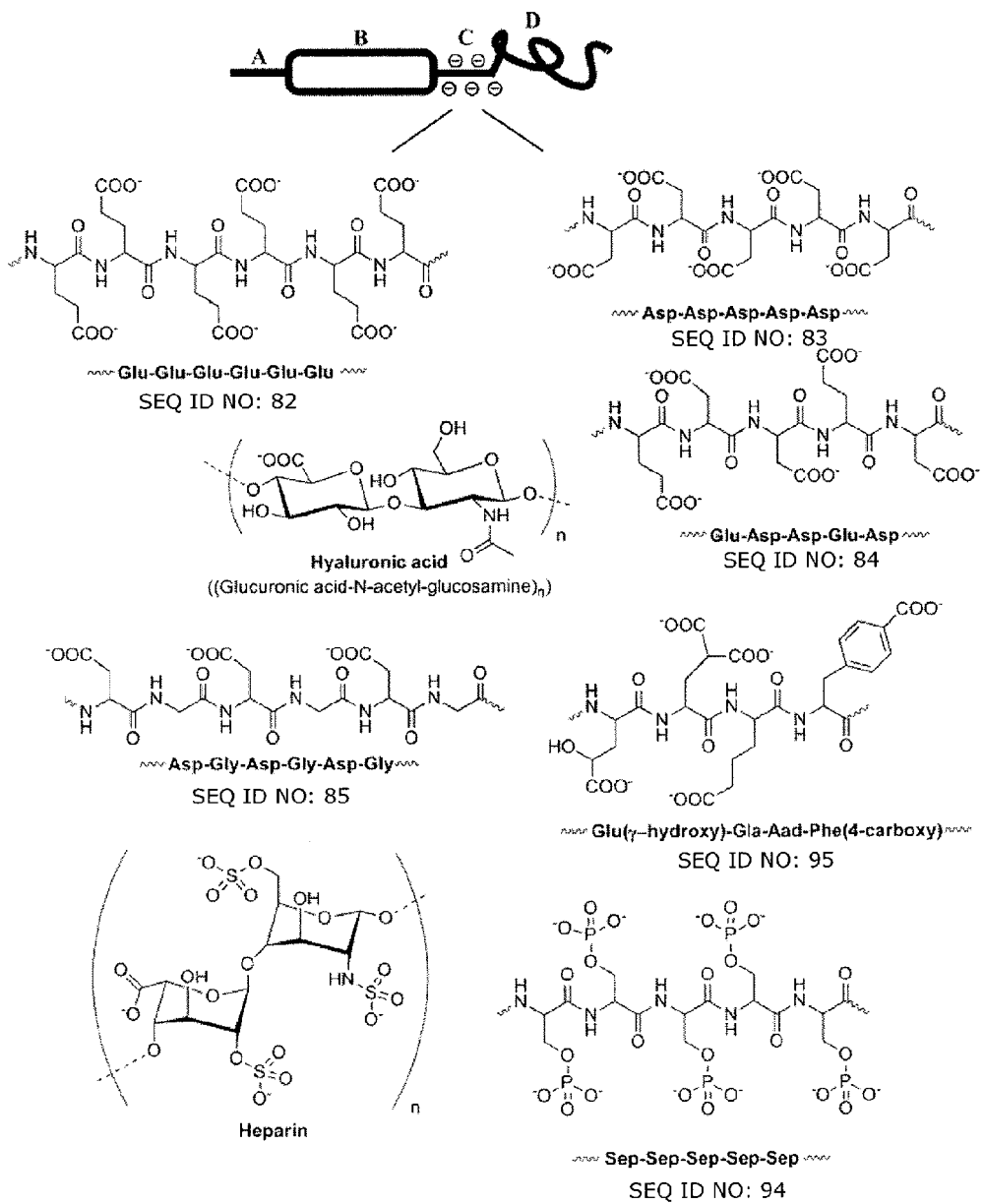
FIG. 6 illustrates a wide range of negatively charged (at pH 6) sequences which could be suitable for the anionic moiety C in the molecules with the general structure A-B-C(-D).

Examples of suitable C fragment are illustrated in FIG. 6. Further suitable examples are disclosed in US 2007/0041904 A1.

The Polymer Moiety

The polymer moiety, D, which is an optional moiety, will, if present, induce long circulating properties of the nanoparticle in mammalian tissue. This may be important so as to ensure that a sufficient amount of the nanoparticle is not degraded or cleared before it reaches the tissue of interest.

Illustrative examples of polymer moieties are those derived from hydrophilic polymers, e.g. poly(alkylene glycols) such as polyethylene glycol, polypropylene glycols, poly(ethylene-co-propylene glycols); glycerins such as glycerin, glycerin ester, and polyglycerins such as diglycerin, triglycerin, teteraglycerin, pentaglycering, hexaglycerin. An additional example is dextrans etc. Among the before-mentioned, poly(alkylene glycols) are preferred, in particular polyethylene glycol.

The weight average molecular weight of such polymers is not particularly critical, but is typically in the range of from 250 Da to 100 kDa, e.g. from 500 Da to 50 kDa, or from 750 Da to 20 kDa, such as in the range of 1 kDa to 10 kDa.

Targeting Ligand

The nanoparticles (e.g. liposomes, lipid coated solid colloid) may further be functionalized with surface targeting moieties that targets selectively expressed and/or over-expressed receptors in cancerous or inflammatory tissue (see under the discussion of the linker B), allowing enhanced accumulation in the diseased tissue or altered pharmacokinetics where the nanoparticles accumulate faster and/or to a higher extend in the diseased tissue through the targeting. Such surface targeting moiety may be added as an additional component E to the compound A-B-C(-D) at any position within the molecule e.g. A-E-B-C(-D), A-B-E-C(-D), A-B-C-E(-D) or A-B-C(-D)-E. Among the before-mentioned, A-B-C(-D)-E is the preferred combination.

Targeting of the nanoparticles (e.g. liposomes, lipid coated solid colloid) can equally be achieved by incorporation of a PEGylated lipid modified at any position with the targeting ligand into the membrane, however exposing the targeting ligand at the distal end of the polymer are preferred.

Examples of such surface targeting moieties are antibodies that specifically recognize a malignant tumor cell or matrix metalloproteinase. As the antibody, a monoclonal antibody is preferred. For example, one kind of monoclonal antibody directed to a single epitope may be used, or a combination of two or more kinds of monoclonal antibodies having specificity for various epitopes may also be used. Moreover, the antibody may be a monovalent antibody or a multivalent antibody, and a naturally occurring type (intact) molecule, or a fragment or derivative thereof may be used. For example, a fragment such as F(ab') 2, Fab' and Fab may be used, and a chimeric antibody or hybrid antibody having at least two of antigen- or epitope-binding sites, a double specificity recombinant antibody such as quadrome and triome, an interspecies hybrid antibody, an anti-idiotype antibody and a chemically modified or processed version of these considered as a derivative of any of the foregoing antibodies may also be used. Further, those that may be used include, for example, an antibody obtained by a synthetic or semi synthetic technique with applying a known cell fusion or hybridoma technique or a known antibody engineering technique, an antibody prepared by using a DNA recombinant technique by applying a conventional technique known from a viewpoint of antibody production, and an antibody having a neutralization or binding property for a target epitope.

The Compounds

The compounds of the invention include the anchoring moiety, A, the cleavable linker, B, the anionic moiety, C, optionally the polymer moiety, D, and optionally the targeting ligand, E. All these constituents as well as embodiments thereof are thoroughly discussed above.

In one currently preferred embodiment, the compound is of the formula A-B-C-D, wherein
A designates an anchoring moiety selected from hydrophobic lipid moieties such as saturated diacyl phospholipids, unsaturated diacyl phospholipids, diacyl glycerols and derivatives thereof, sterols and ceramides, wherein the anchoring moiety A can be composed of a single or multiply copies of the these moieties as well as mixtures thereof;
B designates a cleavable linker selected from peptides which can be activated by proteases and pH sensitive linkers, such as vinyl ethers, orthoesters, acetals, and ketals;
C designates an anionic moiety selected from anionic peptides or anionic polymers such as dextran sulfate, heparin, and hyaluronan, having a net charge of at least −1 at pH 6.0; and
D designates a polymer moiety selected from hydrophilic polymers, such as poly(ethylene glycol), dextran, hyaluronan, polyalcohols, and polycarboxylates.

In another currently preferred embodiment, the compound is of the formula A-B-C-D-E, wherein
A designates an anchoring moiety selected from hydrophobic lipid moieties such as saturated diacyl phospholipids, unsaturated diacyl phospholipids, diacyl glycerols and derivatives thereof, sterols, and ceramides, wherein the anchoring moiety A can be composed of a single or multiply copies of the these moieties as well as mixtures thereof;
B designates a cleavable linker selected from peptides which can be activated by proteases and pH sensitive linkers, such as vinyl ethers, orthoesters, acetals, and ketals;
C designates an anionic moiety selected from anionic peptides or anionic polymers such as dextran sulfate, heparin, and hyaluronan, having a net charge of at least −1 at pH 6.0;
D designates a polymer moiety selected from hydrophilic polymers, such as poly(ethylene glycol), dextran, hyaluronan, polyalcohols, and polycarboxylates; and
E designates a targeting ligand moiety selected from tissue specific ligands such as antibodies, peptides, aptamers, affibodies, and carbohydrates, that target over-expressed receptors in diseased tissue;
and wherein the average net charge of the compounds is at least −1 at pH 6.0.

In another currently preferred embodiment, the compound is of the formula A-B-C, wherein
A designates an anchoring moiety selected from hydrophobic lipid moieties such as saturated diacyl phospholipids, unsaturated diacyl phospholipids, diacyl glycerols and derivatives thereof, sterols, and ceramides, wherein the anchoring moiety A can be composed of a single or multiply copies of the these moieties as well as mixtures thereof;
B designates a cleavable linker selected from peptides which can be activated by proteases and pH sensitive linkers, such as vinyl ethers, orthoesters, acetals, and ketals; and
C designates an anionic moiety selected from anionic peptides or anionic polymers such as dextran sulfate, heparin, and hyaluronan, having a net charge of at least −1 at pH 6.0; and
and wherein the average net charge of the compounds is at least −1 at pH 6.0.

The compounds of the invention are i.a. useful for the preparation of self-organized nanoparticles, e.g. of the types described further above, for drug delivery of small drugs and biologics such as peptides and proteins, oligonucleotides such as siRNA or DNA or RNA, for modification of surface supported membranes in e.g. sensor technologies, diagnostic technology and as an additive for oral delivery of poorly water soluble therapeutics.

Preparation of the Compounds

Molecules with the general formula A-B-C(-D) can be obtain using different synthetic protocols. In one embodiment the A-B-C(-D) can be obtained by combining the individual fragments in a linear approach by reacting the hydrophobic moiety A with the linker B using e.g. Michael addition, Click chemistry, amide-, ester, ether, disulfide bond formation, followed by covalent attachment of the anionic moiety C and, if needed the D fragment, by the above mentioned techniques.

In one currently very interesting embodiment the A-B-C(-D) molecule can be synthesized solely on solid phase support by using standard Fmoc chemistry. In this case, a linear synthetic approach starting from C (or D if needed) is preferred. This approach enables fast convenient synthesis with a high degree of flexibility. When needed, the polymer D can be incorporated by using a TentaGel-PAP resin (Rapp Polymere, Germany) or by the method described by Jølck et al. (Bioconjugate Chem. (2010) 21, 807-810). A synthetic route of this type is further illustrated in the Examples. In both approaches the hydrophobic moiety A can be achieved by mono-, di- or tri-acyalation/alkylation with hydrophobic lipid moieties such as saturated and unsaturated alkyl chains, fatty acids, phospholipids, lysolipids, sterols, ceramides, nanorods and the like. The anchoring moiety A can be composed of a single or multiply copies of the above listed moieties or mixtures thereof. A can also be incorporated as a hydrophobic or semi-hydrophobic polymer e.g. polystyrene (PS), poly (methyl methacrylate) (PMMA), polyphenylene oxide (PPO), polycaprolactone (PCL) and the like or any copolymer/block copolymer including the before mentioned polymers.

Purification of the compounds can be achieved by various means such as dialysis, extraction, chromatography (column chromatography, planar chromatography, paper chromatography, thin layer chromatography, liquid chromatography (reverse phase, normal phase), affinity chromatography, supercritical fluid chromatography, ion exchange chromatography, size-exclusion chromatography).

Preparation of the Self-Organized Nanoparticles

In one embodiment, the nanoparticle has a lipid membrane structure, e.g. a liposome or micelle. The method for preparing such lipid membrane structures is not particularly limited, and the lipid membrane structure in the form of dried mixture can be produced by, for example, once dissolving all the components of the lipid membrane structure in an organic solvent such as chloroform and then subjecting the resulting solution to solidification under reduced pressure by using an evaporator or spray drying by using a spray dryer.

The form of the lipid membrane structure dispersed in an aqueous solvent can be prepared by adding the aforementioned dried mixture to an aqueous solvent and emulsifying the mixture by using an emulsifier such as a homogenizer, ultrasonic emulsifier, high pressure jet emulsifier or the like. Further, the aforementioned form can also be prepared by a method known as a method for preparing liposomes, for example, the reverse phase evaporation method or the like. When it is desired to control a size of the lipid membrane structure, extrusion (extrusion filtration) can be performed under high pressure by using a membrane filter of uniform pore sizes or the like.

The composition of the aqueous solvent (dispersion medium) should not be particularly limited, and examples include, for example, a buffer such as phosphate buffer, citrate buffer, and phosphate-buffered physiological saline, physiological saline, a medium for cell culture and the like. Although the lipid membrane structure can be stably dispersed in these aqueous solvents (dispersion media), the solvents may be further added with a saccharide (aqueous solution), for example, a monosaccharide such as glucose, galactose, mannose, fructose, inositol, ribose and xylose, disaccharide such as lactose, sucrose, cellobiose, trehalose and maltose, trisaccharide such as raffinose and melezitose, and polysaccharide such as cyclodextrin, sugar alcohol such as erythritol, xylitol, sorbitol, mannitol, and maltitol, or a polyhydric alcohol (aqueous solution) such as glycerin, diglycerin, polyglycerin, propylene glycol, polypropylene glycol, ethylene glycol, diethylene glycol, triethylene glycol, polyethylene glycol, polyethylene glycol, ethylene glycol mono-alkyl ether, diethylene glycol mono-alkyl ether and 1,3-butylene glycol. In order to stably store the lipid membrane structure dispersed in such an aqueous solvent (dispersion medium) for a long period of time, it is desirable to minimize electrolytes in the aqueous solvent (dispersion medium) from a viewpoint of physical stability such as prevention of aggregation. Furthermore, from a viewpoint of chemical stability of lipids, it is desirable to control pH of the aqueous solvent (dispersion medium) to be in a range of from weakly acidic pH to around neutral pH (pH 3.0 to 8.0), and to remove dissolved oxygen by nitrogen bubbling.

Further, the dried or frozen form in which the lipid membrane structure is dispersed in an aqueous solvent can be produced by drying or freezing the aforementioned lipid membrane structure dispersed in an aqueous solvent by an ordinary drying or freezing method based on lyophilization or spray drying. When a lipid membrane structure dispersed in the aqueous solvent is first prepared and then successively dried, it becomes possible to store the lipid membrane structure for a long period of time. In addition, when an aqueous solution containing a medicinally active ingredient is added to the dried lipid membrane structure, the lipid mixture is efficiently hydrated and thereby the medicinally active ingredient can be efficiently retained in the lipid membrane structure, which provides an advantageous effect.

When lyophilization or spray drying is carried out, the use of a saccharide (as an aqueous solution), for example, a monosaccharide such as glucose, galactose, mannose, fructose, inositol, ribose and xylose, disaccharide such as lactose, sucrose, cellobiose, trehalose and maltose, trisaccharide such as raffinose and melezitose, and polysaccharide such as cyclodextrin, or a sugar alcohol such as erythritol, xylitol, sorbitol, mannitol, and maltitol may achieve stable storage of the lipid membrane structure for a long period of time. For the freezing, a use of the aforementioned saccharide (as an aqueous solution) or a polyhydric alcohol (aqueous solution) such as glycerin, diglycerin, polyglycerin, propylene glycol, polypropylene glycol, ethylene glycol, diethylene glycol, triethylene glycol, polyethylene glycol, ethylene glycol mono-alkyl ether, diethylene glycol mono-alkyl ether and 1,3-butylene glycol may achieve stable storage of the lipid membrane structure for a long period of time. A saccharide and a polyhydric alcohol may be used in combination. The concentration of the saccharide or polyhydric alcohol in the form in which the lipid membrane structure is dispersed in an aqueous solvent is not particularly limited. In a state that the lipid membrane structure is dispersed in an aqueous solvent, for example, the concentration of the saccharide (aqueous solution) is preferably 2 to 20 percent (W/V), more preferably 5 to 10 percent (W/V), and the concentration of the polyhydric alcohol (aqueous solution) is preferably 1 to 5 percent (W/V), more preferably 2 to 2.5 percent (W/V). When a buffer is used as the aqueous solvent (dispersion medium), the concentration of the buffering agent is preferably 5 to 50 mM, more preferably 10 to 20 mM. The concentration of the lipid membrane structure in an aqueous solvent (dispersion medium) should not be particularly limited. However, the concentration of the total amount of lipids in the lipid membrane structure is preferably 0.1 to 500 mM, more preferably 1 to 100 mM.

In order for the compound of formula A-B-C(-D) to contribute sufficiently to the overall charge of the nanoparticle, it is typically included in an amount of at least 1% by total weight of the constituents making up the self-organized nanoparticle. More typical amounts are 1-40% by weight, such as 2-30% by weight, or 4-25% by weight.

The composition of the vesicles may be modified by post-insertion of lipids and/or lipo-peptides (e.g. the compounds of the invention) producing liposomes with a bilayer asymmetry. Utilizing the post insertion method, liposomes may be decorated on the outer monolayer exclusively e.g. by PEGylated lipids, lipid anchored fluorophores, peptide moieties or combinations of these. As an example, liposomes having no build in trigger or activation mechanism a priori can be modified/upgraded by post insertion of compounds of the invention yielding a vesicle carrier which can be activated by e.g. MMPs.

Drug Delivery Systems

The present invention also provides a drug delivery system comprising a self-organized nanoparticle as defined herein having included in the interior thereof a pharmaceutically active agent and/or a diagnostically relevant species.

It is envisaged that a number of pharmaceutically active agents and diagnostically relevant species can be effectively transported in the vascular system of a mammal by means of the drug delivery system described herein.

In the context of the present invention, the term "mammal" is used in its ordinary meaning, i.e. including humans, pigs, cows, dogs, sheep, goats, monkeys, etc.

Examples of pharmaceutically active agents (in short "drugs"; broadly interpreted as agents which are able to modulate the biological processes of a mammal) include small drugs (e.g. doxorubicin, cisplatin, oxaloplatin, 5-FU), plasmid DNA (e.g. for gene therapy), mRNA, siRNA, peptides and proteins. a) chemotherapeutic agents such as doxorubicin, mitomycin, paclitaxel, nitrogen mustards, etoposide, camptothecin, 5-fluorouracil, etc.; b) radiation sensitizing agents such as porphyrins for photodynamic therapy, or 10B clusters or 157Gd for neutron capture therapy; or c) peptides or proteins that modulate apoptosis, the cell cycle, or other crucial signaling cascades. These drugs can be formulated as a single drug or as a combination of two or more of the above mentioned drugs.

As an alternative, or in addition to inclusion of a pharmaceutically active agent, the drug delivery system may include diagnostically relevant species.

Diagnostically relevant species may be useful for in vivo imaging purposes, and the species may be a compound labeled with a positron-emitting isotope (e.g., $^{18}$F or $^{64}$Cu) for positron emission tomography (PET), gamma-ray isotope (e.g., $^{99m}$Tc) for single photon emission computed tomography (SPECT), a paramagnetic molecule or nanoparticle (e.g., $Gd^{3+}$ chelate or coated magnetite nanoparticle) for magnetic resonance imaging (MRI), a near-infrared fluorophore for near-infra red (near-IR) imaging, a luciferase (firefly, bacterial, or coelenterate) or other luminescent molecule for bioluminescence imaging, or a perfluorocarbon-filled vesicle for ultrasound. Radioactive species, for example a radioactive isotope such as $^{211}$At, $^{131}$I, $^{125}$I, $^{90}$Y, $^{186}$Re, $^{188}$Re, $^{153}$Sm, $^{212}$Bi, $^{32}$P, radioactive isotopes of Lu, and others, may also be included. Alternatively, the species include a fluorescent moiety, such as a fluorescent protein, peptide, or fluorescent dye molecule. Common classes of fluorescent dyes include xanthenes such as rhodamines, rhodols and fluoresceins, and their derivatives; bimanes; coumarins and their derivatives such as umbelliferone and aminomethyl coumarins; aromatic amines such as dansyl; squarate dyes; benzofurans; fluorescent cyanines; carbazoles; dicyanomethylene pyranes, polymethine, oxabenzanthrane, xanthene, pyrylium, carbostyl, perylene, acridone, quinacridone, rubrene, anthracene, coronene, phenanthrecene, pyrene, butadiene, stilbene, lanthanide metal chelate complexes, rare-earth metal chelate complexes, and derivatives of such dyes. Typical fluorescein dyes include 5-carboxyfluorescein, fluorescein-5-isothiocyanate and 6-carboxyfluorescein; examples of other fluorescein dyes can be found, for example, in U.S. Pat. No. 6,008,379, U.S. Pat. No. 5,750,409, U.S. Pat. No. 5,066,580, and U.S. Pat. No. 4,439,356. The species may also include a rhodamine dye, such as, for example, tetramethylrhodamine-6-isothiocyanate, 5-carboxytetramethyl-rhodannine, 5-carboxy rhodol derivatives, tetramethyl and tetraethyl rhodamine, diphenyldimethyl and diphenyldiethyl rhodamine, dinaphthyl rhodamine, rhodamine 101 sulfonyl chloride (sold under the tradename of TEXAS RED), and other rhodamine dyes. The species may alternatively include a cyanine dye, such as, for example, Cy3, Cy3B, Cy3.5, Cy5, Cy5.5, Cy.

In one intriguing embodiment, the drug delivery system has retained therein an antitumor agent or a gene for gene therapy of malignant tumors.

The term "retain" used herein means that the antitumor agent and/or gene is present in the membrane of the nanoparticle, on a surface of the membrane, in an internal space of the membrane, in a lipid layer and/or on a surface of lipid layer of the membrane structure. When the nanoparticle is a liposome, the antitumor agent and/or the gene can also be encapsulated in the inside of the nanoparticle. The amount of the antitumor agent and/or gene to be retained in the nanoparticle is not particularly limited, and the amount may be that sufficient for effectively expressing pharmacological activity thereof in an organism (or in cells). The type of the antitumor agent and/or the gene is not also particularly limited, and may be suitably determined depending on type of malignant tumor, form of the lipid membrane structure, and the like.

Examples of the antitumor agent include, for example, camptothecin derivatives such as irinotecan hydrochloride, nogitecan hydrochloride, exatecan, RFS-2000, lurtotecan, BNP-1350, Bay-383441, PNU-166148, IDEC-132, BN-80915, DB-38, DB-81, DB-90, DB-91, CKD-620, T-0128, ST-1480, ST-1481, DRF-1042 and DE-310, taxane derivatives such as docetaxel hydrate, paclitaxel, IND-5109, BMS-184476, BMS-188797, T-3782, TAX-1011, SB-RA-31012, SBT-1514 and DJ-927, ifosfamide, nimustine hydrochloride, carboquone, cyclophosphamide, dacarbazine, thiotepa, busulfan, melphalan, ranimustine, estramustine phosphate sodium, 6-mercaptopurine riboside, enocitabine, gemcitabine hydrochloride, carmofur, cytarabine, cytarabine ocphosphate, tegafur, doxifluridine, hydroxycarbamide, fluorouracil, methotrexate, mercaptopurine, fludarabine phosphate, actinomycin D, aclarubicin hydrochloride, idarubicin hydrochloride, epirubicin hydrochloride, daunorubicin hydrochloride, doxorubicin hydrochloride, pirarubicin hydrochloride, bleomycin hydrochloride, zinostatin stimalamer, neocarzinostatin, mytomycin C, bleomycin sulfate, peplomycin sulfate, etoposide, vinorelbine tartrate, vincristine sulfate, vindesine sulfate, vinblastine sulfate, amrubicin hydrochloride, gefitinib, exemestan, capecitabine, TNP-470, TAK-165, KW-2401, KW-2170, KW-2871, KT-5555, KT-8391, TZT-1027, S-3304, CS-682, YM-511, YM-598, TAT-59, TAS-101, TAS-102, TA-106, FK-228, FK-317, E7070, E7389, KRN-700, KRN-5500, J-107088, HMN-214, SM-11355, ZD-0473 and the like.

The gene means a nucleic acid, and may be any of oligonucleotide, DNA, and RNA, and examples thereof include a gene that exhibits anti-malignant tumor action upon in vivo expression, for example, a gene for gene therapy of malignant tumor, and the like. Examples of the gene for gene therapy include an antisense oligonucleotide, antisense DNA, antisense RNA, shRNA, and siRNA involved in angiogenesis or cell proliferation in malignant tumor, a gene coding for a physiologically active substance such as enzymes and cytokines, antisense RNA, shRNA, or siRNA, and the like.

When the drug delivery system contains a gene, it is preferable to add a compound having a gene transfer function as a component of the lipid membrane structure to efficiently introduce the gene into a cell. Examples of such a compound include O,O'—N-didodecanoyl-N-(alpha-trimethylammonioacetyl)-diethanolamine chloride, O,O'—N-ditetradecanoyl-N-(alpha-trimethylammonioacetyl)-diethanolamine chloride, O,O'—N-dihexadecanoyl-N-(alpha-trimethylammonioacetyl)-diethanolamine chloride, O,O'—N-dioctadecenoyl-N-(alpha-trimethylammonioacetyl)-diethanolamine chloride, O,O',O"-tridecanoyl-N-(omega-trimethylammonio-decanoyl)aminomethane bromide, N-[alpha-trimethylammonioacetyl]-didodecyl-D-glutamate, dimethyldioctadecylammonium bromide, 2,3-dioleoyloxy-N-[2-(sperminecarboxamido)ethyl]-N,N-dimethyl-1-propane ammonium trifluoroacetate, 1,2-dimyristyloxypropyl-3-dimethylhydroxyethylammonium bromide, 3-beta-[N—(N', N'-dimethylaminoethane)carbamoyl]-cholesterol, and the like. A form is preferred in which any of the compounds having the gene transfer function is present (binds) in a membrane, on a surface of membrane, in a internal space of membrane, in a lipid layer and/or on a surface of lipid layer of the lipid membrane structure.

The lipid membrane structure of the present invention retaining an antitumor agent and/or a gene can be used as a pharmaceutical composition for therapeutic treatment of a malignant tumor. The existing form of the pharmaceutical composition of the present invention and methods for preparation thereof are not particularly limited, and the composition may be produced in the same form as the aforementioned lipid membrane structure. For example, examples of the form include a dried mixture form, a form of dispersion in an aqueous solvent, and a form obtained by drying or freezing the previously mentioned form.

The form of dried mixture can be produced by once dissolving the components of the lipid membrane structure and an antitumor agent and/or a gene in an organic solvent such as chloroform to obtain a mixture, and then subjecting the mixture to solidification under reduced pressure by using an evaporator or spray drying by using a spray dryer. Several methods are known as methods for producing a mixture of lipid membrane structures and a medicinally active ingredient such as an antitumor agent and/or a gene in the form of dispersion in an aqueous solvent. It is possible to appropriately choose a suitable method depending on the mode of retaining an antitumor agent and/or a gene, properties of the mixture and the like of the lipid membrane structure as follows.

Drugs or reactive agents can be loaded into the aqueous core or the lipid membrane of the liposomal carrier depending on the hydrophobicity of the agent. Hydrophobic agents like amphotericin B can be premixed with the lipid components of the carrier before the hydration step, or loaded into the lipid carrier after sizing of the vesicles by partitioning from an aqueous phase. Encapsulation of reactive agents in the aqueous core of the liposome can be achieved by passive or remote loading strategies. By passive encapsulation of e.g. cisplatin, carboplatin, oxaliplatin, Fluorouracil or combinations of these, the reactive agents are solubilized in high concentration in the buffer which is used for hydration of the lipid film. Upon hydration, the multilamellar vesicles containing the active agent are sized (by methods described above) and non-encapsulated reactive agent is removed by dialysis, cross-flow filtration or size exclusion chromatography. An alternative approach for passive loading into the aqueous core of the liposomal carrier subsequent to sizing of the carrier can be facilitated by increasing the membrane permeability towards the active agent by raising the temperature e.g. above the main phase transition ($T_m$) of the lipid membrane or by mild agitation of the carrier e.g. by bath sonication. The non-encapsulated reactive agent is subsequently cleared by methods described above. Alternatively, remote loading strategies utilizing transmembrane pH gradients may be employed for encapsulation of weak lipophilic bases like doxorubicin. Briefly, the lipid material constituting the liposomal carrier is hydrated in a weakly acidic buffer with a high buffer capacity e.g. 250 mM $(NH_4)_2SO_4$. The multilamellar vesicles are subsequently sized (by methods described above) and the buffer on the exterior of the liposomes is exchanged with a mild alkaline buffer to establish the transmembrane pH gradient. The reactive agent is mixed with the alkaline buffer containing the liposomal carrier and the drug subsequently permeates the membrane of the carrier in its deprotonated form. When reaching the aqueous core of the liposomal carrier, the reactive agent is protonated and retained. The transmembrane pH gradient is in general adjusted to match the $pK_a$ of the reactive agent. The following compounds and compound families are suitable for remote loading: Chemotherapeutics—anthracyclines, camptothecins, vinc-alkaloids, mitoxanthrone, bleomycin, ciprofloxacin, cytrabine, mitomycin, streptozocin, estramustine, mechlorethamine, melphalan, cyclophosphamide, triethylenethio-phosphoramide, carmustine, lomustine, semustine, hydroxyurea, thioguanine, decarbazine, procarbazine, epirubicin, carcinomycin, N acetyladriamycin, rubidazone, 5-imidodaunomycin, N-acetyldaunomycine, daunoryline; Anti inflammatory drugs—methylprednisolone hemisuccinate, β-methasone, Antioxidant—tempamine; Anti anxiety muscle relaxants—diclofenac, pridinol; Local anesthetics—lidocaine, bupivacaine, dibucaine, tetracaine, procaine; Photosensitizers for photodynamic therapy—benzoporphyrin and its derivatives (e.g., visudyne); Analgesics—opiods, non-steroidal anti-inflammatory drugs (NSAIDs); Antimicrobial medications—pentamidine, azalides; Antipsychotics—chlorpromazine, perphenazine; The antiparkinson agents—budipine, prodipine, benztropine mesylate, trihexyphenidyl, L-DOPA, dopamine; Antiprotozoals—quinacrine, chloroquine, amodiaquine, chloroguanide, primaquine, mefloquine, quinine; Antihistamines—diphenhydramine, promethazine; Antidepressants—serotonin, imipramine, amitriptyline, doxepin, desipramine; Anti anaphylaxis agents—epinephrine; Anticholinergic drugs—atropine, decyclomine, methixene, propantheline, physostigmine; Antiarrhythmic agents—quinidine, propranolol, timolol, pindolol; Fluorescent dyes—acridine orange, fluorescein, carboxyfluorescein; Prostanoids—prostaglandins, thromboxane, prostacyclin.

In addition to small drugs macromolecules such as e.g. DNA, siRNA can be encapsulated in the aqueous lumen of the liposomes. The procedure for the entrapment of plasmid DNA into liposomes entails the preparation of a lipid film from which multilamellar vesicles and, eventually, small unilamellar vesicles (SUV) are produced. SUV are then mixed with the plasmid DNA destined for entrapment and dehydrated. The dry powder is subsequently rehydrated to generate multilamellar "dehydration-rehydration" vesicles (DRV) containing the plasmid DNA. On centrifugation, liposome-entrapped DNA is separated from non-entrapped DNA. The extent of DNA entrapment in DRV liposomes is monitored by measuring the DNA in the suspended pellet and combined supernatants. The easiest way to monitor entrapment is by using radiolabel ($^{32}P$ or $^{32}S$) DNA and size-exclusion chromatography. Entrapment values range between about 20-100%, depending on the amounts of lipid and DNA used and the presence or absence of a cationic charge.

Liposome-mediated gene delivery can also be achieved by formation of lipoplexes. Lipoplex formation are highly dependent of the cationic lipid/neutral lipid ratio, how the liposomes are prepared, the cationic liposome/DNA charge ratio of the complex of cationic liposome and DNA (lipoplex), and the method used to produce the lipoplex. Furthermore, the successful delivery of DNA depends on a number of factors. These include the chemical structure of the cationic reagents, the supramolecular structure of the lipoplex, their interactions with cell membranes, their internalization and intracellular localization, the release of DNA from the cationic carriers, and the role of helper lipids in cationic liposomes. Lipoplexes can be produced by the interaction of a large variety of liposomes and DNA. The liposomes typically contain at least two components: a cationic lipid and a neutral lipid, Cationic lipids are amphiphilic molecules containing a positively charged polar head group linked to a hydrophobic domain. DOPE and cholesterol are often used as neutral lipids. On its own, DOPE forms inverted hexagonal HII (non-bilayer) phase structures at neutral pH and physiologic temperatures. When combined with a cationic lipid, however, it can participate in bilayer formation. When the cationic lipid is laterally phase-separated by interaction with negatively charged molecules or macromolecules, the DOPE may form non-bilayer structures. The latter may facilitate the destabilization of the cellular membranes with which the cationic lipid interacts, possibly mediating the cytoplasmic delivery of nucleic acids. Cholesterol-containing cationic liposomes have been found to be structurally more stable in physiologic media, thereby enabling the lipoplexes to reach their target tissue intact, thereby protecting the DNA from degradation, and eventually facilitating transfection. Formulation of liposomes composed of positive charged lipids have been achieved by standard liposome techniques such as hydration of a lipid film, dehydration-rehydration, ethanolic injection, reverse-phase evaporation or the detergent dialysis techniques. Mixing of DNA/siRNA and positive charged liposomes result in the formation of lipoplex particles by spontaneous self assembly. The complexation of the DNA is critical for the outcome of the lipoplex. Consequently, the concentration, temperature, environment, and kinetics of mixing all are factors that should be considered carefully in any protocol of lipoplex formation. Anionic, neutral or cationic complexes are obtained depending on the ratio of the cationic charges of the lipid and the anionic DNA phosphodiester bonds. It is widely accepted that preparation of lipoplexes with an excess of positive charge confers higher transfection efficiency. It has been proposed that the initial attachment of lipoplexes to mammalian cells is mediated by electrostatic attraction between the complexes with a net positive charge and negatively charged cell-surface proteoglycans. When the complexes are charge-neutral they tend to aggregate into large assemblies that generally result in reduced gene expression.

The use of PEGylated lipopeptides such as RJ111 with the general structure A-B-C(-D) for as a lipid additive in lipoplexes for gene transfection in cells and in vivo has numerous advantages. Addition of the compound in self-assembled lipoplexes enables control of the surface charge—a feature that has been shown in literature to coincide with prolonged systemic circulation and accumulation in disease areas (such as cancerous tumors or inflammation) when administered intravenously in mammals. The advantage of having the negatively charged compound of the invention (such as RJ111) and positively (such as DOTAP or similar lipid with same function) charged lipids as separate entities in the liposome is that the composition can be optimized to particular properties that are wanted. This could be to fine tune systemic stability while maintaining a high transfection potential of the lipoplex. Furthermore, targeting ligands can be added to the lipoplex either by adding lipid anchored targeting molecules (either directly conjugated to the lipid head or to the end of PEG polymer using thiol/maleimide chemistry) to the liposome formulation before solvent removal so that liposomes used for lipoplexes are formed with the targeting ligand attached to the membrane surface. Alternatively, ligands (e.g. thiol-modified) can be added to e.g. maleimide-activated PEG-polymers on the liposome surfaces after liposomes or even after lipoplexes are formed. Targeting ligands such as hyaluronic acid can be added in the lipoplex formation reaction. In this case e.g. with hyaluronic acid its charge can be used to modify the N/P ratio between negatively charged nucleic acids or equivalents and positively charged lipids (e.g. DOTAP). Hereby the size of self-assembled lipoplex can be controlled. Additionally, the last application may also extend beyond targeting ligands and be a charged polymeric or monomeric compound that modifies the self-assembled lipoplex so that certain properties such as small size can be obtained. The compounds A-B-C(-D), e.g. RJ111, fall in to this category and may provide even further functionality i.e. surface coating. Another way to modify the lipoplex formation is to pre-condense nucleic acid with a substance first. This could be e.g. polyethyleneimine or protamine, where condensed nucleic acid nanoparticles are formed so that self-assemblies with lipid film or hydrated liposomes can be formed afterwards.

The nanoparticles described in the present invention can be administered by e.g. parenteral injection (e.g., intravenous, subcutaneous, intraperitoneal, intramuscular, intravascular, intrathecal, intravitreal, infusion, or local), topical (e.g. epicutaneous or inhalational) or enteral (e.g. per oral or rectally). Administration techniques that are optionally employed with the agents and methods described herein, include e.g., as discussed in Goodman and Gilman, The Pharmacological Basis of Therapeutics, current ed.; Pergamon; and Remington's, Pharmaceutical Sciences (current edition), Mack Publishing Co., Easton, Pa.

Applications

The present invention also relates to the drug delivery system described hereinabove for use as a medicament.

Treatment of severe diseases such as cancer and arthritis etc. is one of the fundamental challenges in medical research and the search for new drug delivery technologies in this area is intense and is of great interest to all major pharmaceutical companies worldwide.

The present invention can be used in drug delivery systems for treatment of various types of cancerous diseases associated with malignant neoplasia such as malignant neoplasm of lip, mouth or throat, such as malignant neoplasm of the tongue, the base of tongue, gum, floor of mouth, palate, parotid gland, major salivary glands, tonsil, oropharynx, nasopharynx, piriform sinus, hypopharynx or other parts of lip, mouth or throat or malignant neoplasms of digestive organs such as malignant neoplasms of oesophagus, stomach, small intestine, colon, rectosigmoid junction, rectum, anus and anal canal, liver and intrahepatic bile ducts, gallbladder, other parts of biliary tract, pancreas and spleen, malignant neoplasms of respiratory and intrathoracic organs such as malignant neoplasms of the nasal cavity and middle ear, accessory sinuses, larynx, trachea, bronchus and lung, thymus, heart, mediastinum and pleura, malignant neoplasms of bone and articular cartilage such as malignant neoplasm of bone and articular cartilage of limbs, bone and articular cartilage, malignant melanoma of skin, sebaceous glands and sweat glands, malignant neoplasms of mesothelial and soft tissue such as malignant neoplasm of mesothelioma, Kaposi's sarcoma, malignant neoplasm of peripheral nerves and autonomic nervous system, malignant neoplasm of retroperitoneum and peritoneum, malignant neoplasm of connective and soft tissue such as blood vessels, bursa, cartilage, fascia, fat, ligament, lymphatic vessel, muscle, synovia, tendon, head, face and neck, abdomen, pelvis or overlapping lesions of connective and soft tissue, malignant neoplasm of breast or female genital organs such as malignant neoplasms of vulva, vagina, cervix uteri, corpus uteri, uterus, ovary, Fallopian tube, placenta or malignant neoplasms of male genital organs such as malignant neoplasms of penis, prostate, testis, malignant neoplasms of the urinary tract, such as malignant neoplasms of kidney, renal pelvis, ureter, bladder, urethra or other urinary organs, malignant neoplasms of eye, brain and other parts of central nervous system such as malignant neoplasm of eye and adnexa, meninges, brain, spinal cord, cranial nerves and other parts of central nervous system, malignant neoplasms of thyroid and other endocrine glands such as malignant neoplasm of the thyroid gland, adrenal gland, parathyroid gland, pituitary gland, craniopharyngeal duct, pineal gland, carotid body, aortic body and other paraganglia, malignant neoplasms of head, face and neck, thorax, abdomen and pelvis, secondary malignant neoplasm of lymph nodes, respiratory and digestive organs, kidney and renal pelvis, bladder and other and urinary organs, secondary malignant neoplasms of skin, brain, cerebral meninges, or other parts of nervous system, bone and bone marrow, ovary, adrenal gland, malignant neoplasms of lymphoid, haematopoietic and related tissue such as Hodgkin's disease, follicular non-Hodgkin's lymphoma, diffuse non-Hodgkin's lymphoma, peripheral and cutaneous T-cell lymphomas, non-Hodgkin's lymphoma, lymphosarcoma, malignant immunoproliferative diseases such as Waldenström's macroglobulinaemia, alpha heavy chain disease, gamma heavy chain disease, immunoproliferative small intestinal disease, multiple myeloma and malignant plasma cell neoplasms such as plasma cell leukaemia, plasmacytoma, solitary myeloma, lymphoid leukaemia such as acute lymphoblastic leukaemia, myeloid leukaemia, monocytic leukaemia, blast cell leukaemia, stem cell leukaemia, and other and unspecified malignant neoplasms of lymphoid, haematopoietic and related tissue such as Letterer-Siwe disease, malignant histiocytosis, malignant mast cell tumor, true histiocytic lymphoma or other types of malignant neoplasia. Carcinoma in situ is also considered as a disease associated with undesirable cell growth. According to the present invention, a disease associated with undesirable cell growth may be carcinoma in situ of oral cavity, oesophagus, stomach, digestive organs, middle ear and respiratory system, melanoma in situ, carcinoma in situ of skin, carcinoma in situ of breast, carcinoma in situ of female or male genitals, carcinoma in situ of bladder, urinary organs or eye, thyroid and other endocrine glands, or other types of carcinoma in situ.

Another application of the present invention is treatment of an inflammatory disease, preferably selected from the group consisting of rheumatoid arthritis, Crohn's disease, multiple sclerosis, and psoriasis. The inflammatory disease can also be selected from the group consisting of inflammatory bowel disease (IBD) including ulcerative colitis and Crohn's disease; surgical adhesions; periodontal disease; polycystic kidney disease; chronic inflammatory diseases of the respiratory tract including asthma, chronic obstructive pulmonary disease (COPD), chronic bronchitis, asthmatic bronchitis, chronic obstructive bronchitis, and emphysema and other diseases which lead to chronic airway obstruction; diseases associated with the obstruction of body passageways, including for example, vascular diseases, neoplastic obstructions, inflammatory diseases, and infectious diseases; and, neovascular diseases of the eye including for example, corneal neovascularization, neovascular glaucoma, proliferative diabetic retinopathy, retrolental fibroblasia and macular degeneration.

Hence, the invention also relates to the drug delivery system described hereinabove for use as a medicament for the treatment of a cancerous or inflammatory condition in a mammal.

Moreover, invention also relates to a method of treating a cancerous or inflammatory condition in a mammal, said method comprising the administration of the drug delivery system described hereinabove to said mammal.

Another application is in biomedical imaging where the present invention can be used to label tissues with over-expressed enzymes or other pathological conditions.

EXAMPLES

Example 1

Liposome Charge Reversal by Peptidase

Materials

Figure 12:
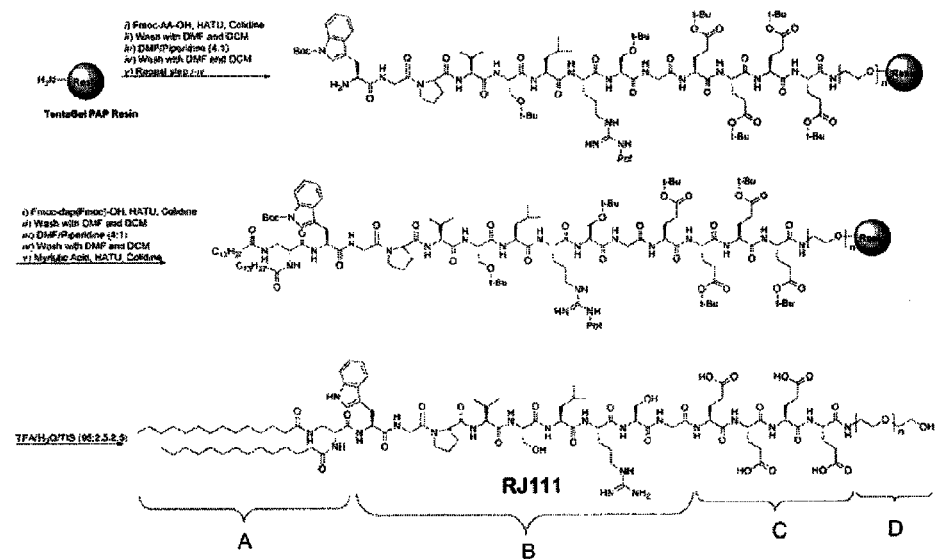
FIG. 12 illustrates the synthesis of RJ111, a peptide based compound of formula A-B-C(-D).

Chemicals were purchased from Sigma-Aldrich Inc. (Brøndby, Denmark) unless otherwise stated. RJ111 was synthesized by solid phase synthesis (FIG. 12). DOTAP (N-[1-(2,3-dioleyl)propyl]-N,N,N-trimethylammonium chloride), POPC (1-palmitoyl-2-oleoyl-sn-glycero-3-phophocholine) were purchased from Avanti Polar Lipids Inc (Alabaster, Ala., USA).

Synthesis

RJ111 with the general structure $(C_{14})_2$-dap-Trp-Ile-Pro-Val-Ser-Leu-Arg-Ser-Gly-Glu-Glu-Glu-Glu-PEG$_{2000}$-OH, where "$(C_{14})_2$-dap" equals "A", "Trp-Ile-Pro-Val-Ser-Leu-Arg-Ser-Gly" (SEQ ID NO: 80) equals "B", "Glu-Glu-Glu-Glu" (SEQ ID NO: 81) equals "C", "PEG$_{2000}$-OH" equals "D" and "dap" is diaminopropionic acid, was synthesized by standard solid phase peptide synthesis (SPPS) methodology using the TentaGel-PAP resin (Rapp Polymere GmbH, Germany, loading 0.34 mmol/g resin) equipped with acid labile PEG$_{2000}$-polymer. Each coupling was achieved using 4 equivalents of fluorenylmethyloxycarbonyl (Fmoc)-protected amino acid, 3.95 equivalents of O-(7-azabenzotriazol-1-yl)-1,1,3,3-tetramethyluronium hexafluorophosphate (HATU) and 8 equivalents of 2,4,6-colidine in N,N-dimethylformamide (DMF) for 45 min. Cleavage of the Fmoc group was achieved by 20% piperidine in DMF for 2×5 min. Each acylation and de-protection step was monitored by the Kaiser ninhydrin test to ensure completion of each reaction step. Diacylation of the immobilized peptide was achieved by acylation of the N-terminal with 2 equivalents $N_\alpha,N_\beta$-di-Fmoc-L-2,3-diaminopropionic acid (Fmoc-Dap(Fmoc)-OH), followed by removal of the Fmoc-protection groups resulting the two free amino groups. Diacylation was achieved in presence of 8 equivalents of myristic acid, 7.90 equivalents of HATU and 16 equivalents 2,4,6-colidine in $CH_2Cl_2$/DMF (1:1) for 2 h. Cleavage of the PEGylated lipopeptide from the solid support was achieved after a 3 h treatment with trifluoroacetic acid/triisopropylsilane/water (95:2.5:2.5) resulting in the trifluoroacetic ester at the distal end of the PEG-polymer (C-terminal). Hydrolysis of the trifluoroacetic ester was achieved by stirring the crude product in water for 24 h resulting in a free alcohol. Finally, the PEGylated lipopeptide was purified by RP-HPLC employing a Waters XTerra $C_{18}$ column using a gradient of 54-62% MeCN over 20 min as described in the following. Solvent A: 5% MeCN+0.1% TFA in $H_2O$, Solvent B: 0.1% TFA in MeCN, flow 17 mL/min. UV-detection at 206 and 280 nm. Gradient profile: t=0 min 54% B, t=2 min 54% B, t=22 min, 62% B, t=26 min 62% B, t=26.01 min 54% B and t=30 min 54% B. The product eluted as a broad peak from 11.00-16.00 min. This fraction was reduced in vacou and lyophilized from a mixture of water and MeCN to give a white fluffy powder. The product was characterized by MALDI-TOF MS and the purity verified by analytical HPLC (>98%).

Additional molecules with the overall A-B-C(-D) structure have been synthesized by a similar approach:

RJ157b: $(C_{16})_2$-dap-Trp-Ile-Pro-Val-Ser-Leu-Arg-Ser-Gly-Glu-Glu-Glu-Glu-PEG$_{2000}$-OH, where "$(C_{16})_2$-dap" equals "A", "Trp-Ile-Pro-Val-Ser-Leu-Arg-Ser-Gly"

-continued (SEQ ID NO: 80) equals "B", "Glu-Glu-Glu-Glu"
(SEQ ID NO: 81) equals "C" and "PEG$_{2000}$—OH" equals "D"

RJ157c: (C$_{18}$)$_2$-dap-Trp-Ile-Pro-Val-Ser-Leu-Arg-Ser-Gly-Glu-Glu-Glu-Glu-PEG$_{2000}$—OH, where "(C$_{18}$)$_2$-dap" equals "A", "Trp-Ile-Pro-Val-Ser-Leu-Arg-Ser-Gly" (SEQ ID NO: 80) equals "B", "Glu-Glu-Glu-Glu" (SEQ ID NO: 81) equals "C" and "PEG$_{2000}$—OH" equals "D".

Liposome Preparation

The PEGylated lipopeptide, RJ111, was formulated in 100 nm liposomes containing, DOTAP and POPC in the molar ratios 10:5:85, 10:10:80, 10:15:75 and 10:20:70 using standard thin-film hydration and repeated extrusions. RJ111, DOTAP and POPC were mixed in chloroform:methanol (8:2) and dried to a lipid-film under a gentle stream of nitrogen. The residual organic solvent was removed under reduced pressure overnight. The lipid-film was hydrated by adding HEPES buffer (10 mM, 150 mM NaCl, pH 7.4), yielding a final lipid concentration of 5 mM. The solution was frozen (using dry ice and iso-propanol) and thawed repeatedly 5 times. The multi lamellar vesicles (MLVs) were sized to small unilamellar vesicles (SUVs) by multiple extrusions through 100 nm polycarbonate filters using a mini-extruder (Avanti Polar Lipids Inc, Alabaster, Ala., USA).

Size and ζ-Potential of RJ111 Liposomes Before and after Enzymatic Cleavage

The size and ζ-potential (zeta potential) of RJ111 formulated liposomes were measured before and after enzymatic cleavage of the RJ111 peptide linker using Thermolysin as a model enzyme. RJ111 formulated liposomes were mixed with a buffered solution of Thermolysine yielding final concentrations of: 2.2 mM lipid (220 µM RJ111), 220 µg/ml Thermolysine, 1 uM, ZnCl$_2$ 0.5 mM CaCl$_2$, 30 mM HEPES and 125 mM NaCl. The reaction mixtures containing Thermolysine and RJ111 formulated in liposomes were heated to 37° C. for a period of 12 hours and the size and ζ-potential were subsequently measured in an equi-osmolar solution of 300 mM Glucose, 10 mM HEPES (pH 7.4) and 1 mM CaCl$_2$. The ζ-potential and size of the non-cleaved RJ111 formulations were measured (ZetaPALS, Brookhaven Instruments Corp., Holtsville, N.Y., USA) in an equi-osmolar solution of 300 mM Glucose, 10 mM HEPES (pH 7.4) and 1 mM CaCl$_2$.

Results

Figure 7:
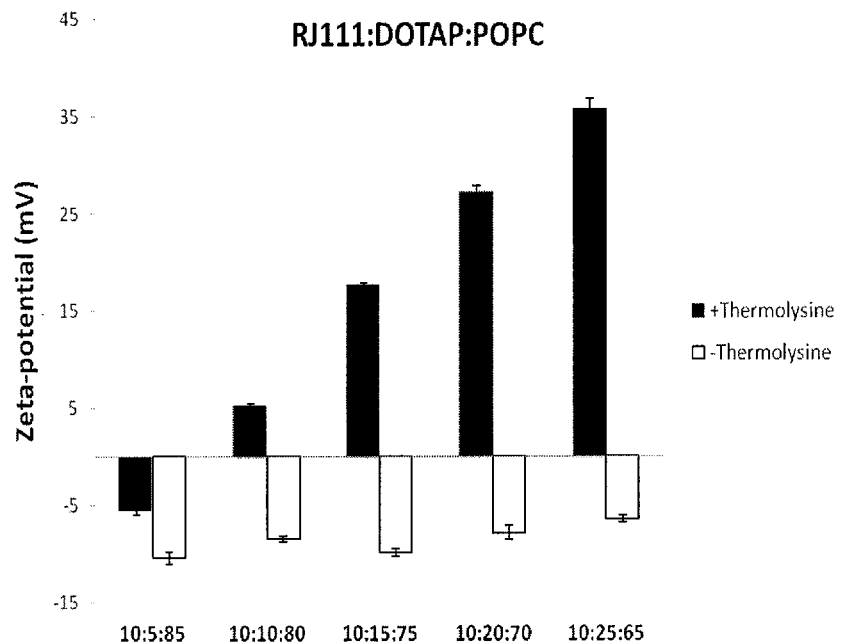
FIG. 7 illustrates the ζ-potential of RJ111-containing liposomes before and after enzymatic cleavage, cf. Example 1.
Figure 8:
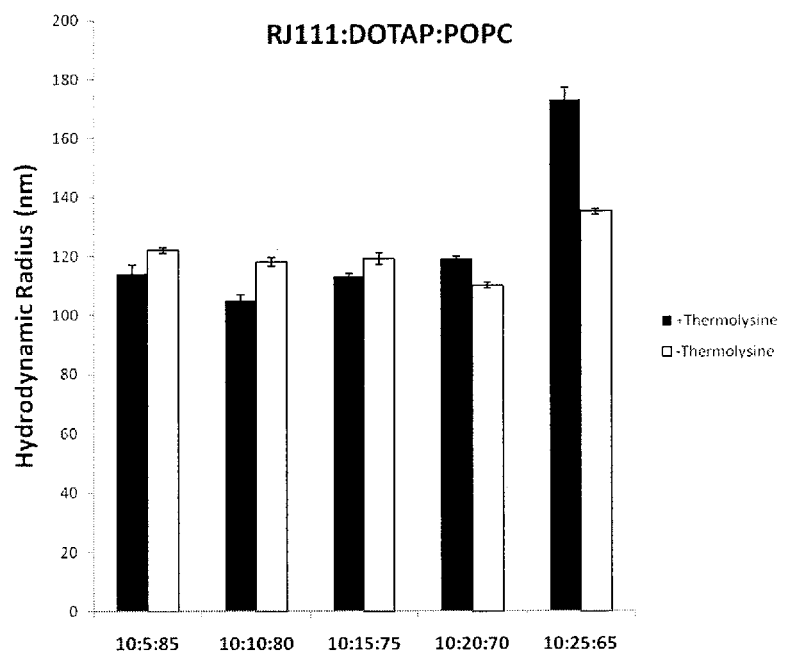
FIG. 8 illustrates the size of RJ111-containing liposomes before and after enzymatic cleavage, cf. Example 1.

The RJ111 formulations are shown to have similar ζ-potential before enzymatic cleavage. Upon activation by Thermolysine, the negatively charged peptide-PEG layer is striped of resulting in exposure of the cationic DOTAP surface which results in an increased ζ-potential as shown in FIG. 7. The ζ-potential of the Thermolysine treated formulations is found to correlate to the molar fraction of DOTAP. The liposome size was checked before and after the Thermolysine treatment and only minor changes was observed as shown in FIG. 8.

Example 2

Transfection with Lipoplex

Materials

Chemicals were purchased from Sigma-Aldrich Inc. (Brøndby, Denmark) unless otherwise stated. RJ111 was synthesized by solid phase synthesis. DOTAP (N-[1-(2,3-dioleyl)propyl]-N,N,N-trimethylammonium chloride), DSPE-PEG2000 (1,2-distearoyl-sn-glycero-3-phosphoethanolamine-N-[methoxy(polyethylene glycol)-2000]), were purchased from Avanti Polar Lipids Inc. (Alabaster, Ala., USA). High quality plasmid, pEGFP-N1 (Clontech, Mountain View, Calif., USA) preparations was made with the Endo-free Giga kit from Qiagen GmbH (Hilden, Germany) according to the manufacturer's instructions. Glassware used for lipid work was washed and rinsed in milliQ water, baked at 180° C. for 6 hours.

Preparation of DOTAP/Cholesterol/RJ111 Liposomes

Chloroform:methanol (9:1) solutions of DOTAP, cholesterol and RJ111 or DSPE-PEG2000 were mixed in a glass tube (12×75 mm) giving 4 different complexes: A. DOTAP:Chol (50:50), B. DOTAP:Chol:RJ111 (50:45:5), C. DOTAP:Chol:RJ111 (50:40:10), D. DOTAP:Chol:DSPE-PEG2000 (50:40:10). While vortexing the solvent was evaporated under a stream of argon gas. High-vacuum drying overnight of the lipid film was followed by hydration in 0.47 ml glucose (5%, D5W) resulting in a 40 mM total lipid solution. The tubes were sealed and placed at 50° C. for 30 minutes with repeated rotary movement to ensure complete hydration of the lipids and left overnight at room temperature. The liposome preparation was placed in a metal basket and sonicated for 2 minutes at 50° C. using a Bransonic water bath (MT-1510, 42 kHz, 80 W, setting "sonics", Branson Ultrasonics, Danbury, Conn., USA) and then downsized using 11 passes in a small-scale extruder (Avanti Polar Lipids Inc, Alabaster, Ala., USA) with polycarbonate nanopore filters (400 nm, 200 nm and 100 nm, Whatman, Frisenette, Knebel, Denmark)) at 50° C.

DNA/Lipoplex Formation and In Vitro Transfection

Adherent HT1080 cells were plated the day prior to the experiment in 12-well plates, 50,000 cells per well as counted in a hemocytometer. Twenty microliters (0.8 µmol) of each liposome preparation were diluted and mixed by rapid pipetting up and down with DNA solutions containing pEGFP-N1 (22.5 µg each) yielding a total volume of 100 µl DNA/lipoplex solution. After 30 min. at RT the DNA/lipoplex (2.25 µg/40 nmol) was added to cells in full growth medium and incubated for 1 day at 37° C. before analysis of reporter activity. Another preparation of the lipoplexes was incubated in 50% conditioned medium (CM) from HT1080 cells for 2 hours prior to addition to cells.

Gene Expression Analysis

Figure 9:
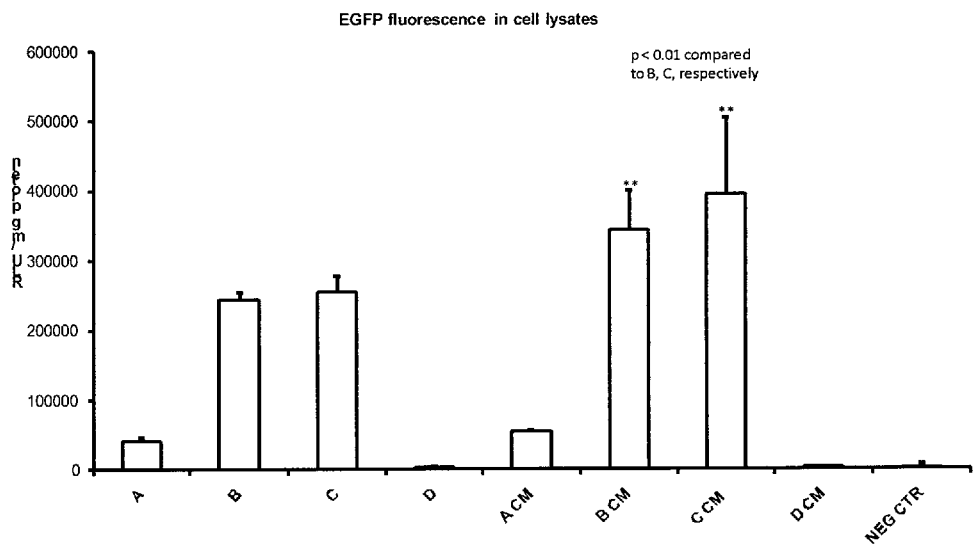
FIG. 9 illustrates the EGFP fluorescence as relative light units (RLU) per milligram protein in the cell lysate, cf. Example 2.

Adherent cells were washed twice with PBS containing heparin (0.125 µg/ml) and lysed in 150 µl reporter buffer containing Na-HEPES (pH 7.4, 50 mM), NaCl (100 mM), EDTA (pH 8.0, 1 mM) and Triton X-100 (1%). One hundred microliters of cell lysate was transferred to a black flat-bottomed microtiter plate and the fluorescence was measured using a microplate reader (Victor3, Perkin Elmer) equipped with appropriate filters for detection of EGFP (Ex. 485±10 nm, Em. 530±10 nm) and rhodamine B (Ex. 530±10 nm, Em. 570±10 nm) fluorescence, respectively. The total protein concentration was measured using 20 µL lysate with the BCA kit (Pierce/Thermo, Rockford, Ill., USA) using bovine serum albumin reference standards, and the absorbance at 570 nm was recorded using Victor3 microplate reader (Dynex Technologies GmbH, Berlin, Germany). EGFP fluorescence was expressed as relative light units (RLU) per milligram protein in the cell lysate (FIG. 9).

The experiment revealed that the lipoplexes containing RJ111 show substantially higher transfection efficiency than the DOTAP:Chol (formulation A), which is known to be a good transfection agent. Also, the protease secreting cell line HT1080 activated complex B and C and this activation was enhanced by pre-incubation in conditioned medium. No transfection was observed for formulation D containing conventional and non-activatable DSPE-PEG2000.

Example 3

Charge Reversal of Lipoplex by Peptidase

Materials

Chemicals were purchased from Sigma-Aldrich Inc. (Brøndby, Denmark) unless otherwise stated. RJ111 was synthesized by solid phase synthesis. DOTAP (N-[1-(2,3-dioleyl)propyl]-N,N,N-trimethylammonium chloride), DSPE-PEG2000 (1,2-distearoyl-sn-glycero-3-phosphoethanolamine-N-[methoxy(polyethylene glycol)-2000]), DOPE-RhB (1,2-dioleoyl-sn-glycero-3-phosphoethanolamine-N-Rhodamine B) were purchased from Avanti Polar Lipids Inc. (Alabaster, Ala., USA).

Preparation of DOTAP/Cholesterol/RJ111 Liposomes

Chloroform:methanol (9:1) solutions of DOTAP, cholesterol and RJ111 or DSPE-PEG2000 were mixed in a glass tube (12×75 mm) giving 4 different complexes: A. DOTAP:Chol:DOPE-RhB (50:49.5:0.5), B. DOTAP:Chol:RJ111:DOPE-RhB (50:44.5:5:0.5), C. DOTAP:Chol:RJ111:DOPE-RhB (50:39.5:10:0.5), D. DOTAP:Chol:RJ111:DOPE-RhB (50:34.5:15:0.5) E. DOTAP:Chol:RJ111:DOPE-RhB (50:29.5:20:0.5). While vortexing the solvent was evaporated under a stream of argon gas. High-vacuum drying overnight of the lipid film was followed by hydration in 0.47 ml glucose (5%, D5W) resulting in a 40 mM total lipid solution. The tubes were sealed and placed at 50° C. for 30 minutes with repeated rotary movement to ensure complete hydration of the lipids and left overnight at room temperature. The liposome preparation was placed in a metal basket and sonicated for 2 minutes at 50° C. using a Bransonic water bath (MT-1510, 42 kHz, 80 W, setting "sonics", Branson Ultrasonics, Danbury, Conn., USA) and then downsized using 11 passes in a small-scale extruder (Avanti Polar) with polycarbonate nanopore filters (400 nm, 200 nm and 100 nm, Whatman, Frisenette, Knebel, Denmark)) at 50° C.

DNA/Lipoplex Formation and In Vitro Transfection

Twenty microliters (0.8 µmol) of each liposome preparation were diluted and mixed by rapid pipetting up and down with DNA solutions containing pEGFP-N1 (22.5 µg each) yielding a total volume of 100 µl DNA/lipoplex solution.

Protease Digestion of Lipoplexes

Lipoplexes were digested with thermolysin by diluting twenty microliters of lipoplex with one volume of HEPES buffered saline (HBS-1), containing NaCl (100 mM), Na-HEPES (50 mM, pH 7.4), $ZnCl_2$ (2 uM), $CaCl_2$ (1 mM). Five microliters of thermolysin (0.4 mg/ml) was added and samples incubated at 37° C. for 2 hours before it was analyzed.

Particle Characterization

Figure 10:
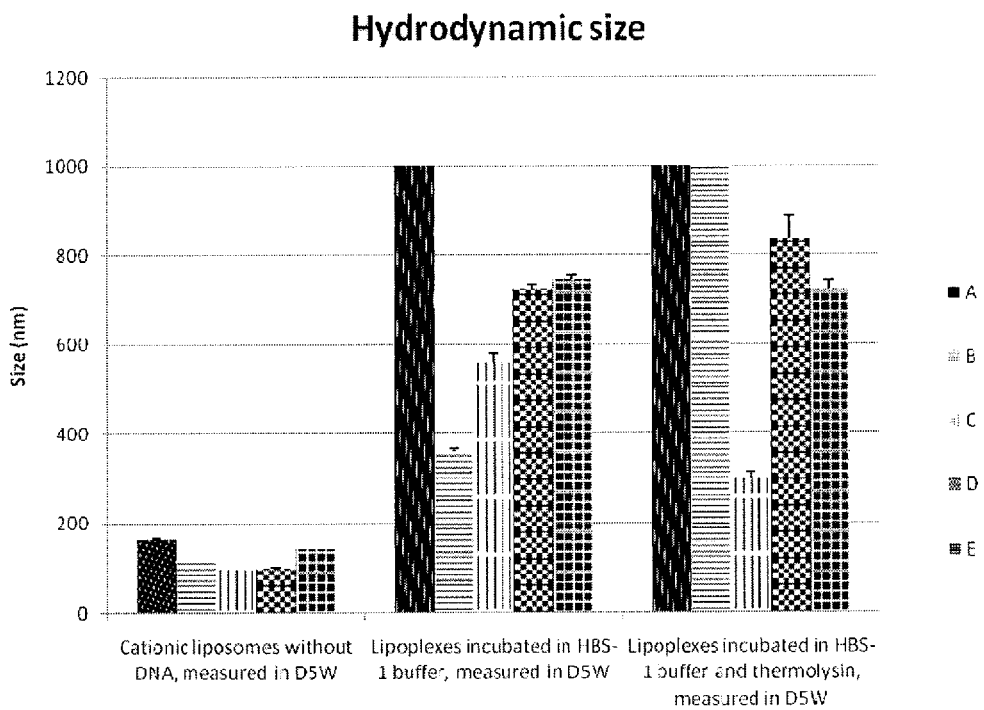
FIG. 10 illustrates the size of RJ111-containing liposomes, cf. Example 3.
Figure 11:
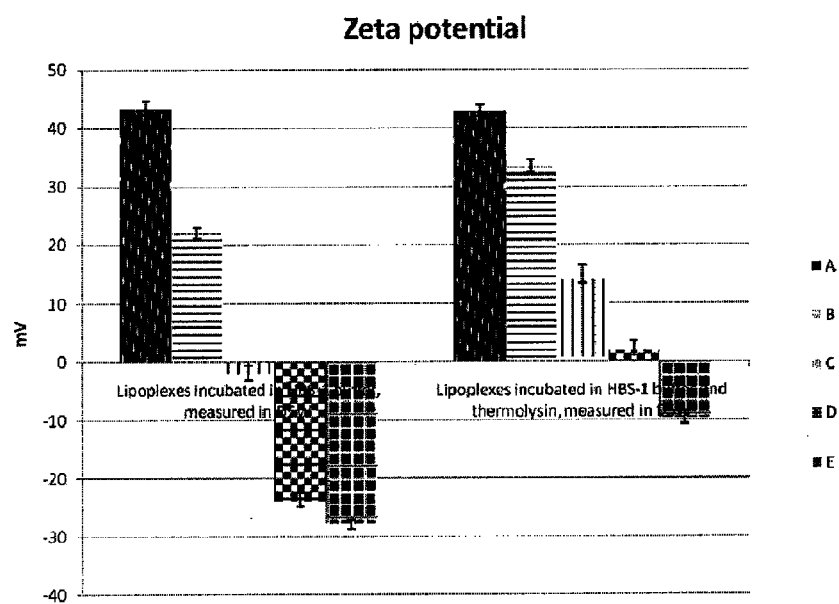
FIG. 11 illustrates the ζ-potential of RJ111-containing liposomes, cf. Example 3.

A ZetaPALS instrument (Brookhaven Instruments Corp., Holtsville, N.Y., USA) was used for characterizing the particle size by dynamic light scattering and ζ-potential. Preparations of liposomes and DNA/lipoplexes were diluted in D5W and placed in a clear disposable cuvette. After degassing, particle size was determined using 10 cycles of 30 s at standard settings. The q size measurements given as the volume-weighted mean diameter were analyzed using cumulant analysis (FIG. 10). Subsequently samples were analyzed for ζ-potential of particles using 10 repeating cycles with confidence p-values less than 0.04 and assessing the quality of measurements by evaluation of the phase plot (FIG. 11).

The measurements shows that the polyplexes are in the sub-micron size range as normally observed with polyplexes. ζ-potential measurements reveal that the charge reversal is effective on polyplexes and that the polyplexes can be activated by proteases.

Example 4

Oxaliplatin Liposomes

Liposome Preparation

The lipopeptid, RJ111, was formulated as 100 nm liposomes with or without encapsulated Oxaliplatin. Both the empty and Oxaliplatin containing lipid formulation (referred to as RJ111 and OxRJ111) were prepared with the composition 5:15:80 RJ111:DOTAP:POPC. A liposome formulation with the composition 5:95 DOPE-PEG2000:POPC containing Oxaliplatin was prepared (referred to as OxPEG2k). Briefly, RJ111, DOTAP, DOPE-PEG2k and POPC were mixed in chloroform:methanol (9:1) in proper scale and dried to a lipid-film under a gentle stream of nitrogen. The residual organic solvent was removed under reduced pressure overnight. The lipid-film was hydrated by adding an aqueous solution, for example a HEPES buffer (10 mM HEPES, 10% Sucrose, 1 mM Calcium Glyconate, pH 7.4), with or without 15 mg/ml Oxaliplatin. The lipid suspension was heated to 65° C. for 60 min and the multi lamellar vesicles (MLVs) were sized to small unilamellar vesicles (SUVs) by multiple extrusions through 100 nm polycarbonate filters using a mini-extruder (Avanti), yielding a final lipid concentration of 55 mM. The liposomes were cooled to room temperature and un-encapsulated Oxaliplatin was removed by dialysis against HEPES buffer (10 mM HEPES, 10% Sucrose, 1 mM Calcium Glyconate, pH 7.4) using Pierce dialysis cassettes with MWCO 12000.

The Oxaliplatin content of the liposomes and the degree of encapsulation was measured by ICP-AES measurements of platinum. Briefly, for each formulation 60 µL liposome formulation was diluted to 3 ml using the hydration buffer (50 fold dilution). Following, 300 µL of the 50 fold diluted sample was further diluted to 3 ml in 1% $HNO_3$ (×10×50) and the 500 fold diluted sample was used to measure the total platinum concentration, CPt total. The remaining 2700 µL (of the 50 fold diluted sample) was loaded on Whatman Vectaspin 3 filters and the filters were spun for 45 min at 1500 g. 600 µL filtrate were collected and diluted to 3 mL using 1% $HNO_3$. The filtrate sample was used to measure the content of platinum in the liposome exterior, CPt exterior. The degree of encapsulation was calculated as DOE=(1-CPt exterior/CPt total)*100%. All lipid formulations had an Oxaliplatin content of 0.8-1.2 mg/mL and a DOE>98%.

Cell Study

The colon cancer cell line HT-1080 was cultured in DMEM medium supplemented with 10% fetal calf serum and 1% Pen-Strep in a humidified atmosphere containing 5% $CO_2$. Cells were plated on 96-well plates at a density of $1 \times 10^4$ cells per well 24 h prior to addition of the tested compounds.

Figure 13:
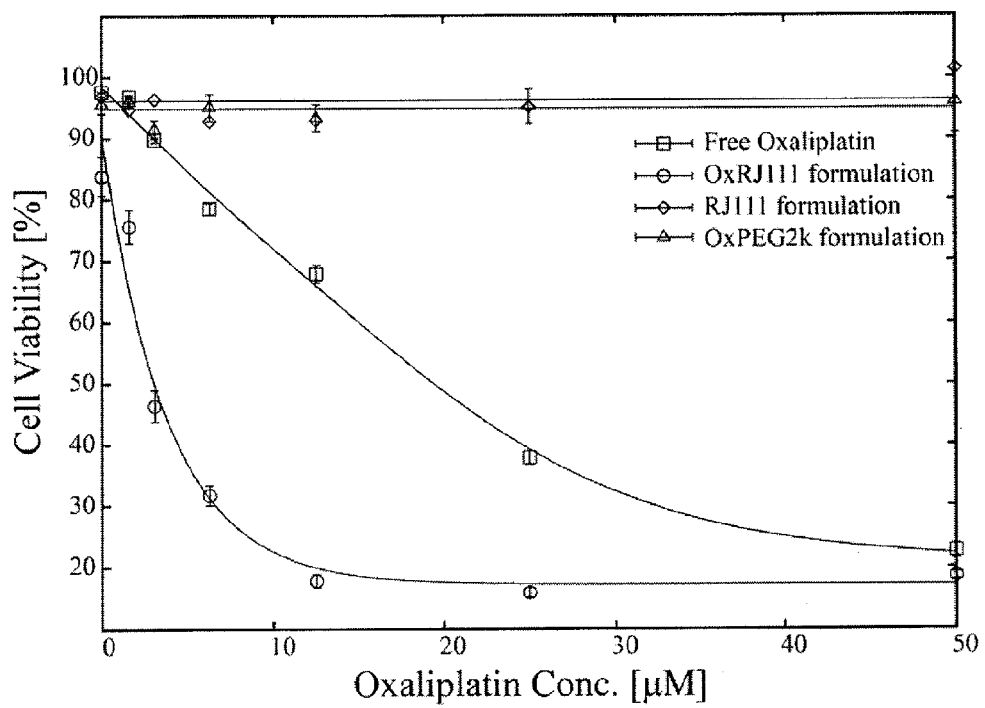
FIG. 13: Cell viability study on HT1080 cells in the presence of free Oxaliplatin, empty RJ111 liposomes (RJ111, 5:15:80 RJ111:DOTAP:POPC), RJ111 liposomes encapsulating Oxaliplatin (OxRJ111, 5:15:80 RJ111:DOTAP:POPC, Oxaliplatin) and liposomes with non-cleavable PEG coat (OxPEG2k, 5:95 DOPE-PEG2000:POPC, Oxaliplatin).

Appropriate amounts of drug-containing media were added to each well, the substances were removed and the cells were washed and incubated in complete medium for another 72 h. Cytotoxic activity was assessed using a XTT assay (XTT, Sigma, St. Louis, USA). Cell viability is expressed as percentage relative to the control (FIG. 13).

The invention claimed is:

1. A nanoparticle selected from the group consisting of a liposome and a lipoplex comprising a compound of the formula A-B-C(-D), wherein
   A designates a hydrophobic lipid anchoring moiety;
   B designates a cleavable linker;
   C designates an anionic moiety having a net charge of from −3 to −30 at pH 6.0; and
   D, which is optional, designates a hydrophilic polymer moiety which induces long circulating properties of the nanoparticle in mammalian tissue;
   wherein the overall net charge of the compound of formula A-B-C-(D) is from −2 to −25 at pH 6.0;
   and wherein the compound of formula A-B-C(-D) is included in an amount of at least 1% by total weight of the nanoparticle.

2. The nanoparticle according to claim 1, wherein the linker B is cleavable in mammalian tissue.

3. The nanoparticle according to claim 1, wherein the linker B is cleavable by external stimuli.

4. The nanoparticle according to claim 1, wherein the linker B is a peptide which is cleavable by a matrix metalloprotease.

5. The nanoparticle according to claim 1, wherein D is present and is a poly(ethylene glycol).

6. The nanoparticle according to claim 1, wherein the nanoparticle is a liposome.

7. The nanoparticle according to claim 1, wherein the nanoparticle is a liposome and wherein the liposome further comprises one or more solid particles in the interior of said liposome.

8. The nanoparticle according to claim 1, wherein the nanoparticle is a lipoplex.

9. A drug delivery system the nanoparticle of claim 1 further comprising a pharmaceutically active agent and/or a diagnostic agent in the interior of the nanoparticle.

10. A method for the administration of a drug delivery system to a mammal in need thereof comprising the step of administering a drug delivery system of claim 9 to said mammal.

11. A compound of compounds of the formula A-B-C-D, wherein
   A designates a hydrophobic lipid anchoring moiety selected from the group consisting of saturated diacyl phospholipids, unsaturated diacyl phospholipids, diacylglycerols and derivatives thereof, sterols, and ceramides;
   B designates a cleavable linker selected from the group consisting of peptides which can be activated by proteases, an S-S linkage, and pH sensitive linkers;

C designates an anionic moiety selected from anionic peptides or anionic polymers, having a net charge of from −3 to −30 at pH 6.0; and D designates a hydrophilic polymer moiety selected from the group consisting of poly(ethylene glycol), dextran, hyaluronan, polyalcohols, and polycarboxylates;

wherein the overall net charge of the compound of formula A-B-C-D is from −2 to −25.

12. A nanoparticle comprising the compound of claim 11, wherein said nanoparticle is a liposome or a lipoplex, and wherein said compound is included in an amount of at least 1% by total weight of the nanoparticle.

13. The nanoparticle according to claim 12, wherein the nanoparticle is a liposome.

14. The nanoparticle according to claim 12, wherein the nanoparticle is a liposome and wherein the liposome further comprises one or more solid particles in the interior of said liposome.

15. A drug delivery system comprising the nanoparticle of claim 12 further comprising a pharmaceutically active agent and/or diagnostically relevant species.

16. A method for the administration of a drug delivery system to a mammal in need thereof comprising the step of administering a drug delivery system of claim 15 to said mammal.

* * * * *

SEQUENCE LISTING

<160> NUMBER OF SEQ ID NOS: 95

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 1

Gly Pro Gln Gly Ile Ala Gly Gln
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 2

Val Pro Met Ser Met Arg Gly Gly
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: extend of
      a released active peptide

<400> SEQUENCE: 3

Ile Pro Val Ser Leu Arg Ser Gly
1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 4

Arg Pro Phe Ser Met Ile Met Gly
1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 5

Val Pro Leu Ser Leu Thr Met Gly
1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: extent of

```
        a released active peptide

<400> SEQUENCE: 6

Ile Pro Glu Ser Leu Arg Ala Gly
1               5

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: extent of
      a released active peptide
<220> FEATURE:
<221> NAME/KEY: misc_feature
<222> LOCATION: (7)..(7)
<223> OTHER INFORMATION: X in position 7 is Nva (Norvaline)

<400> SEQUENCE: 7

Arg Pro Lys Pro Val Glu Xaa Trp Arg Lys
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: extent of
      a released active peptide
<220> FEATURE:
<221> NAME/KEY: misc_feature
<222> LOCATION: (7)..(7)
<223> OTHER INFORMATION: X in position 7 is Nva (Norvaline)

<400> SEQUENCE: 8

Arg Pro Lys Pro Tyr Ala Xaa Trp Met Lys
1               5                   10

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 9

Pro Gln Gly Ile Ala Gly Gln Arg
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 10

Pro Leu Gly Ile Ala Gly Arg
1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: extent of
      a released active peptide
```

```
<400> SEQUENCE: 11

Gly Pro Leu Gly Pro
1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 12

Gly Pro Leu Gly Pro
1               5

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 13

Gly Gly Phe Gly
1

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 14

Gly Phe Gly Gly
1

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 15

Phe Gly Gly Gly
1

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 16

Phe Phe Gly Gly
1

<210> SEQ ID NO 17
<211> LENGTH: 5
```

```
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 17

Gly Gly Gly Phe Gly
1               5

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 18

Gly Gly Phe Phe
1

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 19

Gly Gly Gly Gly Gly Gly
1               5

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 20

Gly Gly Gly Phe
1

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 21

Gly Gly Gly Gly
1

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 22

Gly Gly Leu Gly
```

```
<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 23

Gly Gly Tyr Gly
1

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 24

Gly Gly Val Leu
1

<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 25

Gly Gly Leu Leu
1

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 26

Gly Gly Phe Leu
1

<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 27

Gly Gly Tyr Leu
1

<210> SEQ ID NO 28
<211> LENGTH: 4
<212> TYPE: PRT
<213> ORGANISM: Artificial Sequence
<220> FEATURE:
<223> OTHER INFORMATION: Description of Artificial Sequence: extent of
```

-continued

```
       a released active peptide

<400> SEQUENCE: 28

Gly Gly Val Gln
1

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: extent of
       a released active peptide

<400> SEQUENCE: 29

Gly Gly Leu Gln
1

<210> SEQ ID NO 30
<211> LENGTH: 4
<212> TYPE: PRT
<213> ORGANISM: Artificial Sequence
<220> FEATURE:
<223> OTHER INFORMATION: Description of Artificial Sequence: extent of
       a released active peptide

<400> SEQUENCE: 30

Gly Gly Ile Gln
1

<210> SEQ ID NO 31
<211> LENGTH: 4
<212> TYPE: PRT
<213> ORGANISM: Artificial Sequence
<220> FEATURE:
<223> OTHER INFORMATION: Description of Artificial Sequence: extent of
       a released active peptide

<400> SEQUENCE: 31

Gly Gly Phe Gln
1

<210> SEQ ID NO 32
<211> LENGTH: 4
<212> TYPE: PRT
<213> ORGANISM: Artificial Sequence
<220> FEATURE:
<223> OTHER INFORMATION: Description of Artificial Sequence: extent of
       a released active peptide

<400> SEQUENCE: 32

Gly Gly Tyr Gln
1

<210> SEQ ID NO 33
<211> LENGTH: 4
<212> TYPE: PRT
<213> ORGANISM: Artificial Sequence
<220> FEATURE:
<223> OTHER INFORMATION: Description of Artificial Sequence: extent of
       a released active peptide

<400> SEQUENCE: 33

Gly Gly Trp Gln
1

<210> SEQ ID NO 34
```

```
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 34

Gly Gly Leu Ser
1

<210> SEQ ID NO 35
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 35

Gly Gly Phe Ser
1

<210> SEQ ID NO 36
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 36

Gly Gly Tyr Ser
1

<210> SEQ ID NO 37
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 37

Gly Gly Val Thr
1

<210> SEQ ID NO 38
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 38

Gly Gly Leu Thr
1

<210> SEQ ID NO 39
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 39
```

Gly Gly Phe Thr
1

<210> SEQ ID NO 40
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 40

Gly Gly Tyr Thr
1

<210> SEQ ID NO 41
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 41

Gly Gly Trp Thr
1

<210> SEQ ID NO 42
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 42

Gly Gly Val Met
1

<210> SEQ ID NO 43
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 43

Gly Gly Leu Met
1

<210> SEQ ID NO 44
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 44

Gly Gly Ile Met
1

<210> SEQ ID NO 45
<211> LENGTH: 4
<212> TYPE: PRT
<213> ORGANISM: Artificial Sequence
<220> FEATURE:

```
<223> OTHER INFORMATION: Description of Artificial Sequence: extent of
      a released active peptide

<400> SEQUENCE: 45

Gly Gly Phe Met
1

<210> SEQ ID NO 46
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 46

Gly Gly Tyr Met
1

<210> SEQ ID NO 47
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide
<220> FEATURE:
<221> NAME/KEY: misc_feature
<222> LOCATION: (4)..(4)
<223> OTHER INFORMATION: X in position 4 is Cit (Citrulline)

<400> SEQUENCE: 47

Gly Gly Val Xaa
1

<210> SEQ ID NO 48
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide
<220> FEATURE:
<221> NAME/KEY: misc_feature
<222> LOCATION: (4)..(4)
<223> OTHER INFORMATION: X in position 4 is Cit (Citrulline)

<400> SEQUENCE: 48

Gly Gly Leu Xaa
1

<210> SEQ ID NO 49
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide
<220> FEATURE:
<221> NAME/KEY: misc_feature
<222> LOCATION: (4)..(4)
<223> OTHER INFORMATION: X in position 4 is Cit (Citrulline)

<400> SEQUENCE: 49

Gly Gly Phe Xaa
1

<210> SEQ ID NO 50
<211> LENGTH: 4
```

```
<212> TYPE: PRT
<213> ORGANISM: Artificial Sequence
<220> FEATURE:
<223> OTHER INFORMATION: Description of Artificial Sequence: extent of
      a released active peptide
<220> FEATURE:
<221> NAME/KEY: misc_feature
<222> LOCATION: (4)..(4)
<223> OTHER INFORMATION: X in position 4 is Cit (Citrulline)

<400> SEQUENCE: 50

Gly Gly Tyr Xaa
1

<210> SEQ ID NO 51
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide
<220> FEATURE:
<221> NAME/KEY: misc_feature
<222> LOCATION: (4)..(4)
<223> OTHER INFORMATION: X in position 4 is Cit (Citrulline)

<400> SEQUENCE: 51

Gly Gly Trp Xaa
1

<210> SEQ ID NO 52
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 52

Gly Gly Gly Asn
1

<210> SEQ ID NO 53
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 53

Gly Gly Ala Asn
1

<210> SEQ ID NO 54
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 54

Gly Gly Val Asn
1

<210> SEQ ID NO 55
<211> LENGTH: 4
<212> TYPE: PRT
```

```
<213> ORGANISM: Artificial Sequence
<220> FEATURE:
<223> OTHER INFORMATION: Description of Artificial Sequence: extent of
      a released active peptide

<400> SEQUENCE: 55

Gly Gly Leu Asn
1

<210> SEQ ID NO 56
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 56

Gly Gly Ile Asn
1

<210> SEQ ID NO 57
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 57

Gly Gly Gln Asn
1

<210> SEQ ID NO 58
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 58

Gly Gly Thr Asn
1

<210> SEQ ID NO 59
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 59

Gly Gly Phe Asn
1

<210> SEQ ID NO 60
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 60

Gly Gly Tyr Asn
1
```

```
<210> SEQ ID NO 61
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 61

Gly Gly Met Asn
1

<210> SEQ ID NO 62
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 62

Gly Gly Pro Asn
1

<210> SEQ ID NO 63
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide
<220> FEATURE:
<221> NAME/KEY: misc_feature
<222> LOCATION: (3)..(3)
<223> OTHER INFORMATION: X in position 3 is Cit (Citrulline)

<400> SEQUENCE: 63

Gly Gly Xaa Asn
1

<210> SEQ ID NO 64
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 64

Gly Gly Trp Gly
1

<210> SEQ ID NO 65
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 65

Gly Gly Ser Asn
1

<210> SEQ ID NO 66
<211> LENGTH: 4
<212> TYPE: PRT
```

```
<213> ORGANISM: Artificial Sequence
<220> FEATURE:
<223> OTHER INFORMATION: Description of Artificial Sequence: extent of
      a released active peptide

<400> SEQUENCE: 66

Gly Gly Pro Ala
1

<210> SEQ ID NO 67
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 67

Gly Gly Pro Val
1

<210> SEQ ID NO 68
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 68

Gly Gly Pro Leu
1

<210> SEQ ID NO 69
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 69

Gly Gly Pro Ile
1

<210> SEQ ID NO 70
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 70

Gly Gly Pro Gln
1

<210> SEQ ID NO 71
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 71

Gly Gly Pro Ser
1
```

<210> SEQ ID NO 72
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 72

Gly Gly Pro Tyr
1

<210> SEQ ID NO 73
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 73

Gly Gly Pro Met
1

<210> SEQ ID NO 74
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 74

Gly Gly Met Pro
1

<210> SEQ ID NO 75
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 75

Gly Gly Pro Pro
1

<210> SEQ ID NO 76
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide
<220> FEATURE:
<221> NAME/KEY: misc_feature
<222> LOCATION: (4)..(4)
<223> OTHER INFORMATION: X in position 4 is Cit (Citrulline)

<400> SEQUENCE: 76

Gly Gly Pro Xaa
1

<210> SEQ ID NO 77
<211> LENGTH: 4
<212> TYPE: PRT

```
<213> ORGANISM: Artificial Sequence
<220> FEATURE:
<223> OTHER INFORMATION: Description of Artificial Sequence: extent of
      a released active peptide

<400> SEQUENCE: 77

Gly Gly Ile Leu
1

<210> SEQ ID NO 78
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide
<220> FEATURE:
<221> NAME/KEY: misc_feature
<222> LOCATION: (4)..(4)
<223> OTHER INFORMATION: X in position 4 is Cit (Citrulline)

<400> SEQUENCE: 78

Gly Gly Ile Xaa
1

<210> SEQ ID NO 79
<211> LENGTH: 13
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 79

Trp Ile Pro Val Ser Leu Arg Ser Gly Glu Glu Glu Glu
1               5                   10

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 80

Trp Ile Pro Val Ser Leu Arg Ser Gly
1               5

<210> SEQ ID NO 81
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 81

Glu Glu Glu Glu
1

<210> SEQ ID NO 82
<211> LENGTH: 6
<212> TYPE: PRT
<213> ORGANISM: Artificial Sequence
<220> FEATURE:
<223> OTHER INFORMATION: Description of Artificial Sequence: extent of
      a released active peptide
```

```
<400> SEQUENCE: 82

Glu Glu Glu Glu Glu Glu
1               5

<210> SEQ ID NO 83
<211> LENGTH: 5
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 83

Asp Asp Asp Asp Asp
1               5

<210> SEQ ID NO 84
<211> LENGTH: 5
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 84

Glu Asp Asp Glu Asp
1               5

<210> SEQ ID NO 85
<211> LENGTH: 6
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 85

Asp Gly Asp Gly Asp Gly
1               5

<210> SEQ ID NO 86
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 86

Gly Phe Ser Gly
1

<210> SEQ ID NO 87
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 87

Gly Lys Val Ser
1

<210> SEQ ID NO 88
<211> LENGTH: 4
<212> TYPE: PRT
```

<213> ORGANISM: Artificial Sequence
<220> FEATURE:
<223> OTHER INFORMATION: Description of Artificial Sequence: extent of
      a released active peptide

<400> SEQUENCE: 88

Gly Trp Ile Gly
1

<210> SEQ ID NO 89
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 89

Gly Lys Lys Gly
1

<210> SEQ ID NO 90
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 90

Gly Ala Tyr Met
1

<210> SEQ ID NO 91
<211> LENGTH: 8
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 91

Val Pro Leu Ser Leu Tyr Ser Gly
1               5

<210> SEQ ID NO 92
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 92

Ile Pro Val Ser
1

<210> SEQ ID NO 93
<211> LENGTH: 4
<212> TYPE: PRT
<213> ORGANISM: Artificial Sequence
<220> FEATURE:
<223> OTHER INFORMATION: Description of Artificial Sequence: extent of
      a released active peptide

<400> SEQUENCE: 93

Leu Arg Ser Gly
1

```
<210> SEQ ID NO 94
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(5)
<223> OTHER INFORMATION: Xaa is phosphoserine

<400> SEQUENCE: 94

Xaa Xaa Xaa Xaa Xaa
1               5

<210> SEQ ID NO 95
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is gamma-hydroxy-glutamic acid
<220> FEATURE:
<221> NAME/KEY: MISC_FEATURE
<222> LOCATION: (2)..(2)
<223> OTHER INFORMATION: Xaa is gamma-carboxy-L-glutamic acid
<220> FEATURE:
<221> NAME/KEY: MISC_FEATURE
<222> LOCATION: (3)..(3)
<223> OTHER INFORMATION: Xaa is (S)-2-amino-5-carboxy-pentanoic acid
<220> FEATURE:
<221> NAME/KEY: MISC_FEATURE
<222> LOCATION: (4)..(4)
<223> OTHER INFORMATION: Xaa is 4-hydroxy-phenylalanine

<400> SEQUENCE: 95

Xaa Xaa Xaa Xaa
1
```